United States Patent
Haacke

(10) Patent No.: US 9,008,396 B2
(45) Date of Patent: Apr. 14, 2015

(54) TISSUE SIMILARITY MAPPING

(75) Inventor: E. Mark Haacke, Detroit, MI (US)

(73) Assignee: Magnetic Resonance Innovations, Inc., Detroit, MI (US)

( * ) Notice: Subject to any disclaimer, the term of this patent is extended or adjusted under 35 U.S.C. 154(b) by 274 days.

(21) Appl. No.: 13/458,521

(22) Filed: Apr. 27, 2012

(65) Prior Publication Data

US 2012/0275676 A1 Nov. 1, 2012

Related U.S. Application Data

(60) Provisional application No. 61/481,093, filed on Apr. 29, 2011.

(51) Int. Cl.
| | |
|---|---|
| *G06K 9/00* | (2006.01) |
| *G01R 33/563* | (2006.01) |
| *G06T 7/00* | (2006.01) |
| *A61B 5/00* | (2006.01) |
| *A61B 5/055* | (2006.01) |
| *G01R 33/50* | (2006.01) |

(52) U.S. Cl.
CPC ........ *G01R 33/56308* (2013.01); *G06T 7/0016* (2013.01); *G01R 33/56366* (2013.01); *G06T 2207/10088* (2013.01); *G06T 2207/30016* (2013.01); *A61B 5/004* (2013.01); *A61B 5/055* (2013.01); *G01R 33/50* (2013.01)

(58) Field of Classification Search
None
See application file for complete search history.

(56) References Cited

U.S. PATENT DOCUMENTS

| | | | |
|---|---|---|---|
| 6,556,856 B1 | 4/2003 | Mistretta et al. | |
| 8,089,278 B1 | 1/2012 | Du | |
| 2004/0092809 A1* | 5/2004 | DeCharms | 600/410 |
| 2008/0021304 A1 | 1/2008 | Stemmer | |
| 2008/0081987 A1 | 4/2008 | Miyazaki | |
| 2010/0194390 A1 | 8/2010 | Kannengiesser et al. | |
| 2012/0277572 A1* | 11/2012 | Hubbard | 600/419 |

OTHER PUBLICATIONS

International Search Report and Written Opinion for PCT Application No. PCT/US2012/035569, mailed Aug. 13, 2012, 9 pages.
Adhya S., et al., Pattern of hemodynamic impairment in multiple sclerosis: dynamic susceptibility contrast perfusion MR imaging at 3.0 T. Neuroimage Dec. 2006;33(4): pp. 1029-1035.
Bakshi R., et al., MRI in multiple sclerosis: current status and future prospects. Lancet Neurol Jul. 2008;7: pp. 615-625.
Biswal, B, et al., Functional connectivity in the motor cortex of resting human brain using echo-planar. MRI. Magn. Reson. Med. 1995;34: pp. 537-541.
Boxerman, J.L., et al., Relative cerebral blood volume maps corrected for contrast agent extravasation significantly correlate with glioma tumor grade, whereas uncorrected maps do not. AJNR Am J Neuroradiol 2006;27: pp. 859-867.

(Continued)

*Primary Examiner* — Atiba O Fitzpatrick
(74) *Attorney, Agent, or Firm* — Foley & Lardner LLP

(57) ABSTRACT

A method is disclosed including: receiving a time resolved series of magnetic resonance (MR) images of an imaged region of a subject; processing the images to generate comparison data by comparing a temporal behavior of a reference region of the MR images to at least one other region of the MR images; an generating an output based on the comparison data. The method may be applied in a variety of contexts, including perfusion weighted imaging, determination of T2*, and other time series functions.

22 Claims, 16 Drawing Sheets

(56) References Cited

OTHER PUBLICATIONS

Calamante, F., et al., Nonlinear ΔR2* Effects in Perfusion Quantification Using Bolus-Tracking MRI. Magnetic Resonance in Medicine, 2009;61: pp. 486-492.

Chen J.J., et al., The Impact of Partial-Volume Effects in Dynamic Susceptibility Contrast Magnetic Resonance Perfusion Imaging. Journal of Magnetic Resonance Imaging, 2005;22: pp. 390-399.

Ge Y., et al., Dynamic Susceptibility Contrast Perfusion MR Imaging of Multiple Sclerosis Lesions: Characterizing Hemodynamic Impairment and Inflammatory Activity. AJNR Am J Neuroradiol 2005;26: pp. 1539-1547.

Haacke M., et al., Susceptibility Weighted Imaging (SWI). Magnetic Resonance in Medicine 2004;52: pp. 612-618.

Harris, et al., Dynamic susceptibility contrast MR imaging of regional cerebral blood volume in Alzheimer disease: a promising alternative to nuclear medicine. AJNR Am J Neuroradiol 1998;19: pp. 1727-1732.

Horowitz, B., The elusive concept of brain connectivity. NeuroImage, 2003;19: pp. 466-470.

Inglese, et al., Deep gray matter perfusion in multiple sclerosis: dynamic susceptibility contrast perfusion magnetic resonance imaging at 3 T. Arch Neurol 2007;64(2): pp. 196-202.

Kinuya, et al., Role of brain perfusion single-photon emission tomography in traumatic head injury. Nuclear Medicine Communications 2004;25: pp. 333-337.

Lassmann H., Pathology of Multiple Sclerosis. Section 4, Chapter 10 in McAlpine's Multiple Sclerosis, Third Edition. Churchill Livingstone: London, 1998; pp. 323-358.

Law, et al., Microvascular Abnormality in Relapsing-Remitting Multiple Sclerosis: Perfusion MR Imaging Findings in Normal-appearing White Matter. Radiology Jun. 2004: vol. 231, No. 3; pp. 645-652.

Lorenz et al., Effect of Using Local Arterial Input Functions on Cerebral Blood Flow Estimation. Journal of Magnetic Resonance Imaging. 2006;24: pp. 57-65.

Lucchinetti, et al., Distinct patterns of multiple sclerosis pathology indicates heterogeneity in pathogenesis. Brain Pathology 1996;6: pp. 259-274.

Neema et al., MRI in multiple sclerosis: what's inside the toolbox? Neurotherapeutics: The Journal of the American Society for Experimental NeuroTherapeutics. Oct. 2007;4: pp. 602-617.

Ostergaard L., Principles of cerebral perfusion imaging by bolus tracking. Journal of Magnetic Resonance Imaging, 2005;22: pp. 710-717.

Putnam, T.J., Studies in multiple sclerosis: encephalitis and sclerotic plaques produced by venular obstruction. Archives of Neurology and Psychiatry 1935; 33: pp. 929-940.

Rashid, et al., Abnormalities of cerebral perfusion in multiple sclerosis. J Neurol Neurosurg Psychiatry 2004;75(9): pp. 1288-1293.

Rogowska, et al., Applications of Similarity Mapping in Dynamic MRI. IEE Transactions on Medical Imaging, vol. 14, No. 3, Sep. 1995, pp. 480-486.

Wiart M., et al., Perfusion-Based Segmentation of the Human Brain Using Similarity Mapping. Magnetic Resonance in Medicine 45: 2001; pp. 261-268.

Wittsack, et al., MR Imaging in Acute Stroke: Diffusion-weighted and Perfusion Imaging Parameters for Predicting Infarct Size. Radiology 2002;222: pp. 397-403.

Wuerfel, et al., Changes in cerebral perfusion precede plaque formation in multiple sclerosis: a longitudinal perfusion MRI study. Brain 2004;127(1): pp. 111-119.

* cited by examiner

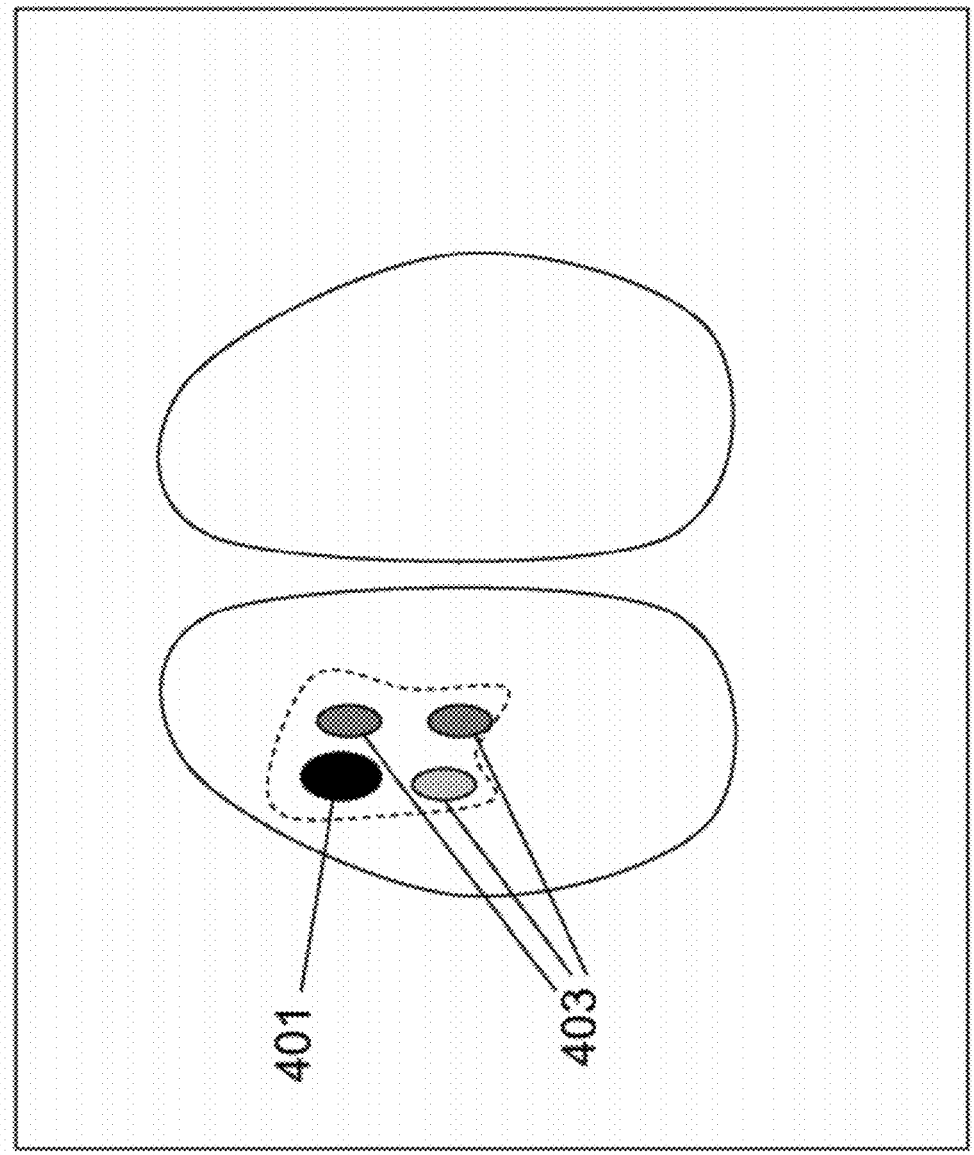

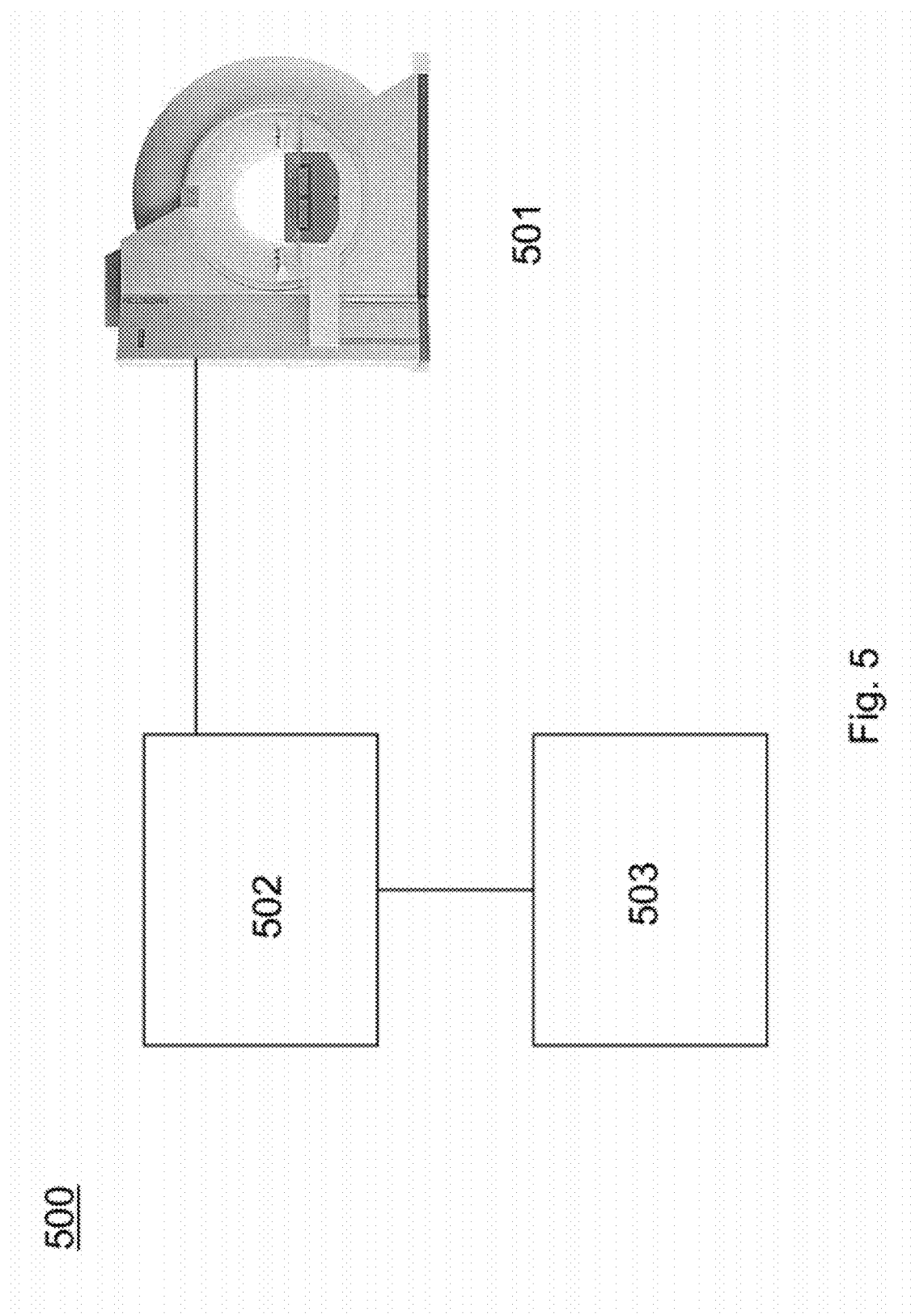

TISSUE SIMILARITY MAPPING

CROSS REFERENCE TO RELATED APPLICATIONS

The application claims the benefit of U.S. Provisional Application No. 61/481,093, filed Apr. 29, 2011, the entire contents of which are incorporated herein by reference.

BACKGROUND

Magnetic resonance (MR) imaging is a useful noninvasive method for imaging the internal components of a wide array of objects. Its noninvasive imaging of tissue in living subjects, especially humans, is highly valued in the medical field.

Time resolved MR scans (e.g., including a series of MR images acquired at different times) of a living subject can measure temporal behavior. For example, a time resolved MR series of scans may be used to detect the temporal behavior of tissue during the inflow and/or outflow of a contrast agent to and/or from the tissue.

SUMMARY

Applicants have appreciated that time resolved MR imaging data may be processed to determine the similarity of various tissues located in an imaged region (e.g., the brain). A time resolved series of images may be processed to compare the temporal behavior of a reference image region to that of one or more other test regions to generate comparison data indicative of the degree of similarity of the temporal behavior. A tissue similarity map (TSM) image may be generated based on this processing, mapping the level of similarity of tissue across the imaged region to the test region.

The techniques described above advantageously leverage the temporal information contained in a time resolved MR imaging scan. For example, a similarity comparison of this type can be used, e.g., to determine information about the tissue in the test regions. For example, multiple sclerosis (MS) lesions in the brain may exhibit a characteristic type of vascular response. If a known MS lesion is chosen as the reference region, the technique described above can be used to generate a map of the brain showing regions which exhibit a similar vascular response behavior. These regions may then be identified as additional regions potentially impacted by MS, even when no MS lesion can be identified at these regions using traditional imaging techniques (i.e., techniques which do not fully leverage the temporal information contained in the scan).

In one aspect, a method is disclosed including: receiving a time resolved series of magnetic resonance (MR) images of an imaged region of a subject; processing the images to generate comparison data by comparing a temporal behavior of a reference region of the MR images to at least one other region of the MR images; an generating an output based on the comparison data.

In some embodiments, the time resolved series of MR images includes a time resolved series of MR images collected at respective times.

In some embodiments, the time resolved images include a two dimensional image.

In some embodiments, the time resolved images includes a three dimensional image.

In some embodiments, the time resolved series of MR images are collected both prior to and during introduction of contrast agent to the imaged region of the subject.

In some embodiments, a portion of the time resolved series of MR images are collected during a time period in which the contrast agent has reached equilibrium in the imaged region of a subject.

Some embodiments include: generating the time resolved series MR images by: receiving MR magnitude, phase, or magnitude and phase data related to the imaged region of the subject at a series of times; for each time, Fourier transforming the corresponding data to generate an image in the series of MR images.

In some embodiments, each of the MR images are generated using a echo based imaging sequence, and where the time resolved series of magnetic resonance (MR) images are acquired at intervals corresponding to the echo time of the imaging sequence.

In some embodiments, the echo based imaging sequence includes at least one from the list consisting of: an echo planar scan and a gradient echo scan.

In some embodiments, the comparing includes: generating error data indicative of a difference between an image value at the reference region and an image value in at least one other region over the time resolved series of MR images; and generating the comparison data based at least in part of the error data.

In some embodiments, generating error data includes: calculating the mean square error between an image value at the reference region and an image value at the at least one other region over the time resolved series of MR images.

In some embodiments, generating error data includes: calculating the absolute difference between an image value at the reference region and an image value at the at least one other region over the time resolved series of MR images.

In some embodiments, processing the images to generate comparison data by comparing a temporal behavior of a reference region of the MR images to at least one other region of the MR images includes: selecting one or more image pixels in the reference region; storing temporally resolved reference pixel data for the selected one or more image pixels; and generating the comparison data by comparing the temporal behavior of one or more other pixels to the stored temporally resolved reference pixel data.

In some embodiments, the comparison data is generated using a limited temporal window.

In some embodiments, the time resolved series of MR images correspond to an MR perfusion study of the imaged region.

In some embodiments, the time resolved series of MR images corresponds to an echo planar scan.

In some embodiments, the imaged region includes a portion of a brain.

In some embodiments, the time resolved series of MR images include information related to a change in tissue in the imaged region occurring during the acquisition of the series.

In some embodiments, the time resolved series of MR images corresponds to a gradient echo scan.

In some embodiments, the MR images contain information related to blood vessels in the imaged region.

Some embodiments include generating information indicative of relative local blood volume based on the comparison data.

Some embodiments include generating information indicative of absolute $T2^*$ based on the comparison data.

Some embodiments include generating information indicative of relative $T2^*$ based on the comparison data.

Some embodiments include receiving reference $T2^*$ information indicative of $T2^*$ for at least one pixel in the time resolved series of MR images; and generating information indicative of relative T2* based on the comparison data and the reference T2* information.

In some embodiments, generating the comparison data includes: selecting at least one reference pixel from the reference region; generating similarity information by comparing a temporal behavior of the reference pixel over the series of MR images at the reference pixel to a temporal behavior of each of substantially all of the remaining pixels in the series of MR images.

In some embodiments, generating the output based on the comparison data includes: generating, based on the similarity information, at least one tissue similarity map image indicative of the comparison of the temporal behavior of the reference pixel over the series of MR images at the reference pixel to the temporal behavior of each of substantially all of the remaining pixels in the series of MR images.

In some embodiments, the comparison data includes: determining at least one low signal pixel in the series of MR images having a signal to noise ratio below a threshold level; and omitting the low signal pixel from the comparison of the temporal behavior of the reference pixel over the series of MR images at the reference pixel to the temporal behavior of each of substantially all of the remaining pixels in the series of MR images.

Some embodiments include: determining, based on the comparison data, similarity information indicative of the similarity between the temporal behavior of the reference region and at least one other region Some embodiments include comparing the similarity information to a threshold.

In some embodiments, the reference region corresponds to an abnormal region of the imaged region.

In some embodiments, the reference region includes at least one selected from the list consisting of: a tumor, a lesion, a region of damaged tissue, and a region experiencing bleeding.

Some embodiments include diagnosing a disease or condition based on the comparison data.

Some embodiments include, based on the comparison data, generating tissue property information indicative of a property of tissue in the imaged region of the subject.

In some embodiments, the tissue property includes at least one selected from the list consisting of: T2*, relative blood volume, relative cerebral blood volume, the presence of a blood vessel, and the presence of a selected tissue type.

Some embodiments include at least partially segmenting the imaged region based on the tissue property information Some embodiments include normalizing each image in the time resolved series of MR images based on at least one reference image in there series.

In some embodiments, the normalization is carried out on a pixel by pixel basis.

In some embodiments, the reference image is the temporally first image in the series.

In another aspect, a system is disclosed including: a processor configured to receive MR image data and process the data using any one of the methods set forth above. Some embodiments include an MR imager in communication with the processor and configured to generate the MR image data.

In another aspect, a computer program product, including a non-transitory computer usable medium having a computer readable program code embodied therein, said computer readable program code adapted to be executed to implement the any one of the methods set forth above.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The drawings are not necessarily to scale, emphasis instead generally being placed upon illustrating the principles of the invention.

FIGS. 4A and 4B show exemplary tissue similarity maps.

FIG. 5 is a schematic of an MRI system.

DETAILED DESCRIPTION

Figure 1:
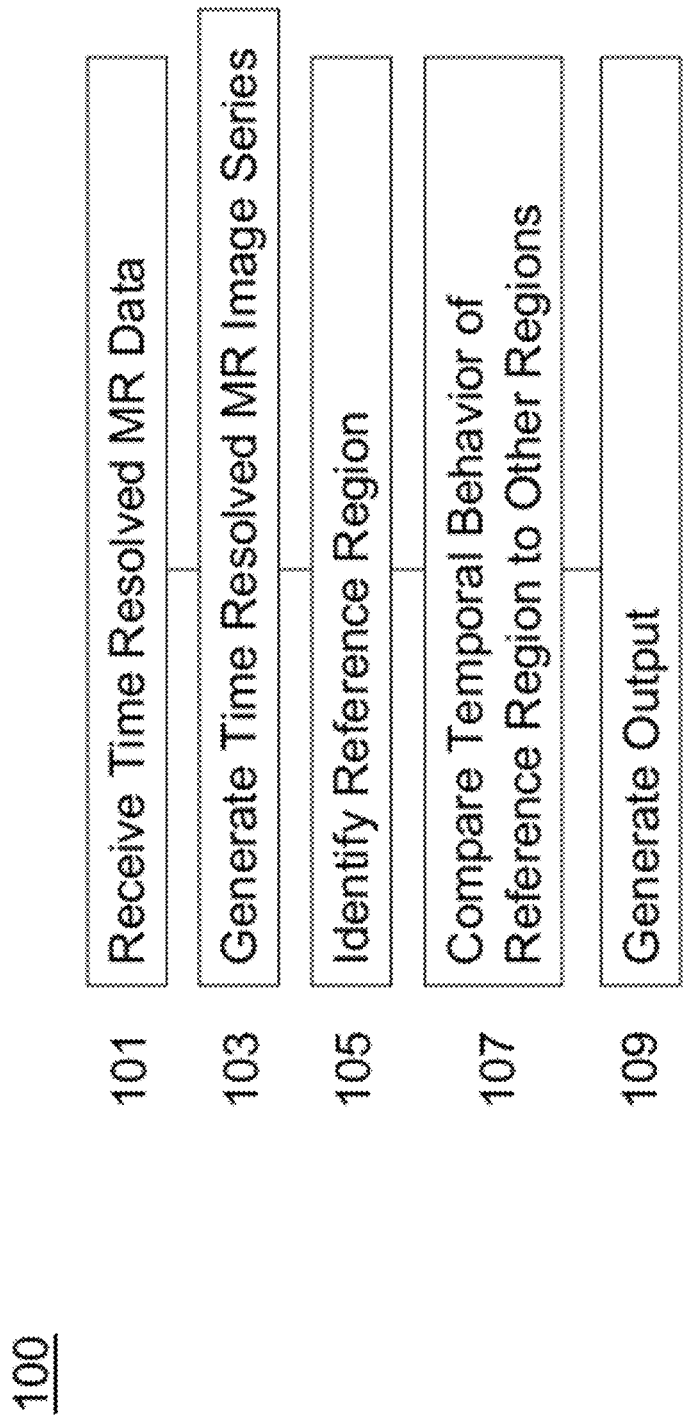
FIG. 1 shows a process for processing time resolve MR data to perform a tissue similarity comparison.

Referring to FIG. 1, an exemplary process 100 for processing time resolved MR data to perform a tissue similarity comparison is illustrated. In step 101 time resolved MR data is received. The data may be received directly from an MR imaging device, from memory storage, or from any other suitable source. The time resolved MR image data may include MR signal magnitude ρ(r), and/or phase, ϕ(r) information a variety of spatial points r (e.g., corresponding to a one dimensional line, two dimensional slice or three dimensional slab) acquired at multiple points in time. The information may be stored, e.g., as a matrix representing the data in one, two, or three dimensions for each time point.

In step 103, the MR information is processed (e.g., Fourier transformed) to generate a time resolved series of images (e.g., magnitude and/or phase images). The time resolved series of images may include one or more one, two, or three dimensional images for each time point in the series. The interval between time points may be any suitable value (e.g., without limitation less than 500 ms, less than 100 ms, less than 50 ms, etc., e.g., in the range of 50 ms-5 s). In some embodiments, the MR data may be obtained using an echo based pulse scheme (e.g., a gradient echo pulse sequence).

Figure 2:
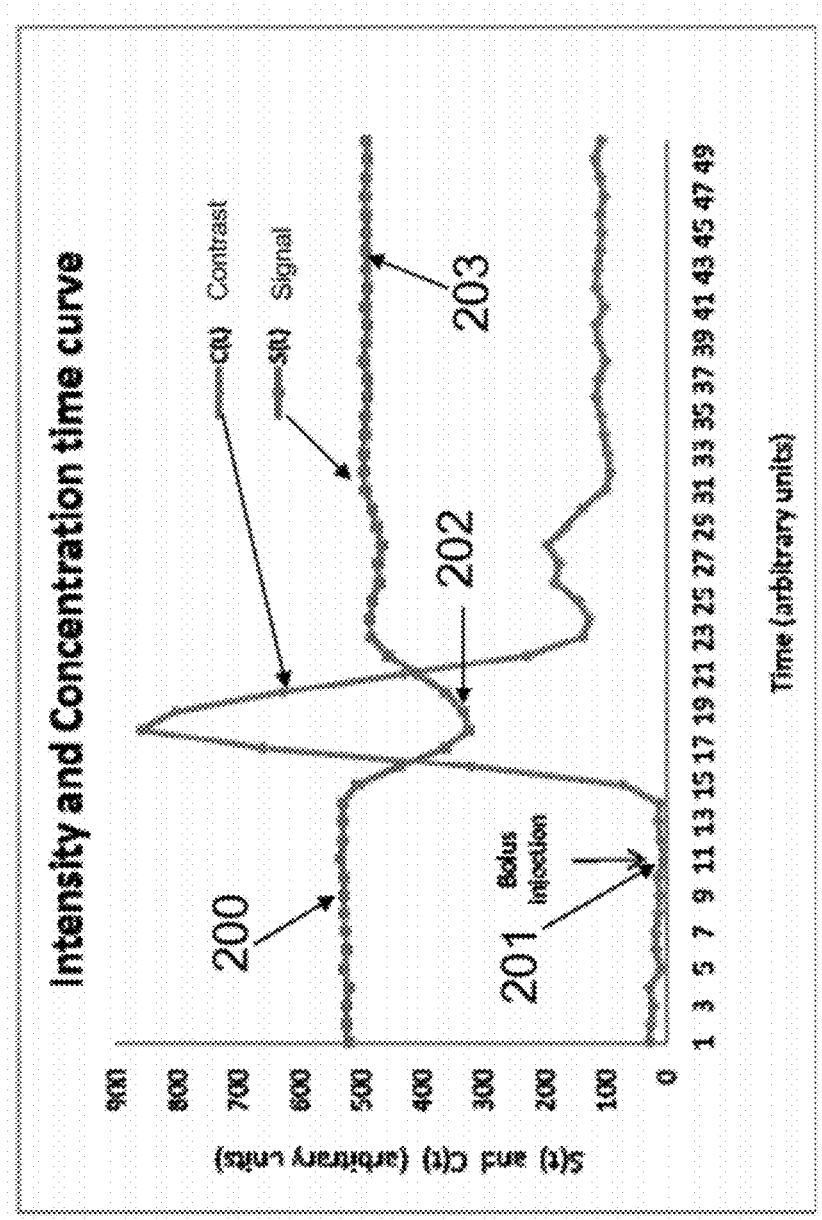
FIG. 2 is a graph illustrating contrast flow in a subject.

In some embodiments, the time resolved series of MR images may be obtained during the introduction of contrast agent to the imaged region. For example, FIG. 2 illustrates the signal and contrast level dependence in a perfusion weighted imaging experiment. The experiment is started prior to injection (level curve 200). After injection (at a time 201), the contrast bolus enters the tissue and the signal drops as the concentration increases (signal behavior shown in 202). The contrast agent slowly washes out and the signal slowly returns to normal (signal level in 203). In various embodiments . . . . In various embodiments, the time resolved series of MR images may include images obtained before injection, during the inflow period, during the equilibrium period, during the outflow period, after the outflow period, or any suitable combination thereof. For example, in some embodiments, the images are acquired over a period that begins prior to injection and continues after the injection. In some embodiments, the images are acquired over a period long enough that at least some of the images correspond to the equilibrium period (i.e., such that these images do not exhibit temporal changes due to contrast agent flow).

It is to be understood that in other embodiments, the techniques described herein may be used with non-contrast imaging processes.

In general, the time resolved series of MR images may include any suitable images generated using any suitable imaging technique. For example, in some embodiments, the MR image series is generated using an echo planar scan which monitors temporal changes in the signal. For example, an echo planar scan can be used to perform a perfusion study (e.g., of the brain). The MR images may be perfusion weighted images, e.g., dynamic susceptibility contrast perfusion weighted images. In some embodiments, the MR image series may be a conventional gradient echo scan, e.g., used to collect data about blood vessels in the head, neck, body, or other region of a subject.

In step 105, a spatial region in the images is identified as a reference region. The reference region may be a single image pixel (or voxel, for three dimensional images), or a number of pixels. The selected region may correspond to a known tissue type (e.g., white matter or grey matter in the brain, a tumor, a lesion, a blood vessel, etc.).

In step 107, the temporal behavior of the reference region is compared to the temporal behavior of at least one other test region. This comparison may be used to generate comparison data indicative of the level of similarity between the temporal behavior of the reference and test regions. In cases where the tissue type (or other information) of the reference region is known, this comparison data may be used to identify the tissue in the test region as like or unlike the reference region. In step 109, an output is generated, e.g., a tissue similarity map (as described in detail below) may be displayed or saved as a data file.

In some embodiments, the reference region can be compared to multiple test regions, e.g., the temporal behavior of a reference pixel may be compared to multiple test pixels covering some portion of or the entire imaged region. These comparisons may be used to generate a tissue similarity map of the region, as discussed in greater detail below.

The comparison of the temporal behavior of the reference region to the test region may be performed using any suitable metric or technique. For example, in some embodiments, the mean square error (MSE) between the MR signal at the reference region $s_{ref}(t)$ and the MR signal at the test region s(t) may be calculated over some or all of the time points in the series. For example, in one embodiment, the MSE may be calculated as:

$$MSE = \sum_{i=1}^{n} (s(t_i - \Delta t) - s_{ref}(t_i))^2$$

where i is an index ranging over some or all of the time points in the series, and Δt is an optional time offset, e.g., to account for different contrast peak times at the different regions. In other embodiments, other metrics may be used including, for example, the absolute value of the difference between the signal, a root mean square difference, a logarithmic difference, etc. In various embodiments, any other known type of comparison may be used. In some embodiments, any other suitable type of optimization scheme may be used to extract information related to the imaged tissue.

Figure 3:
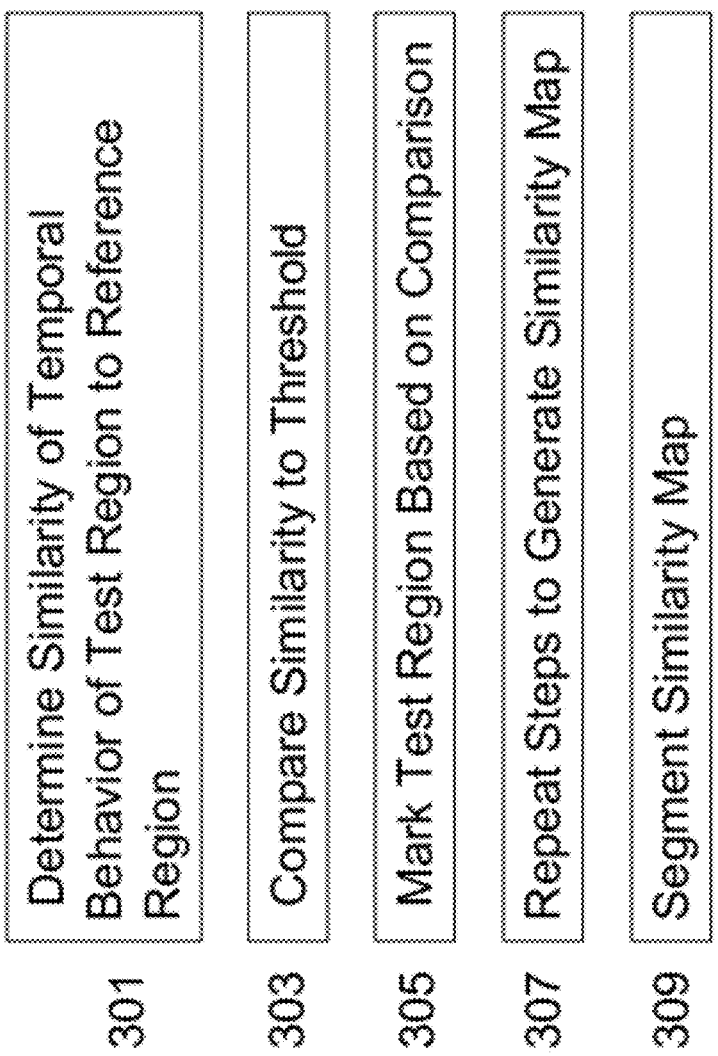
FIG. 3 shows a process for generating a tissue similarity map.

FIG. 3 shows an exemplary process 300 for generating a tissue similarity map (TSM), using the techniques described above. In step 301, the similarity between a reference region and a test region is determined. In step 303, the level of similarity is compared to a threshold level. In step 305, based on this comparison the test region is marked in a TSM image. For example, if the level of similarity is below the threshold, the region may be left blank, effectively nulling out all tissue which is below the similarity threshold. For similarity above the threshold, the region can be marked with some indicia (e.g., color or grey level) representing the level of similarity. In some embodiments, the similarity map may be generated in reverse, e.g., nulling out all tissue which is above a threshold similarity with the reference region, and allowing dissimilar tissue to be identified. In some embodiments, the thresholding step may be omitted, with similarity information (e.g., represented as a color or grayscale level) being presented regardless of the level.

Figure 4A:
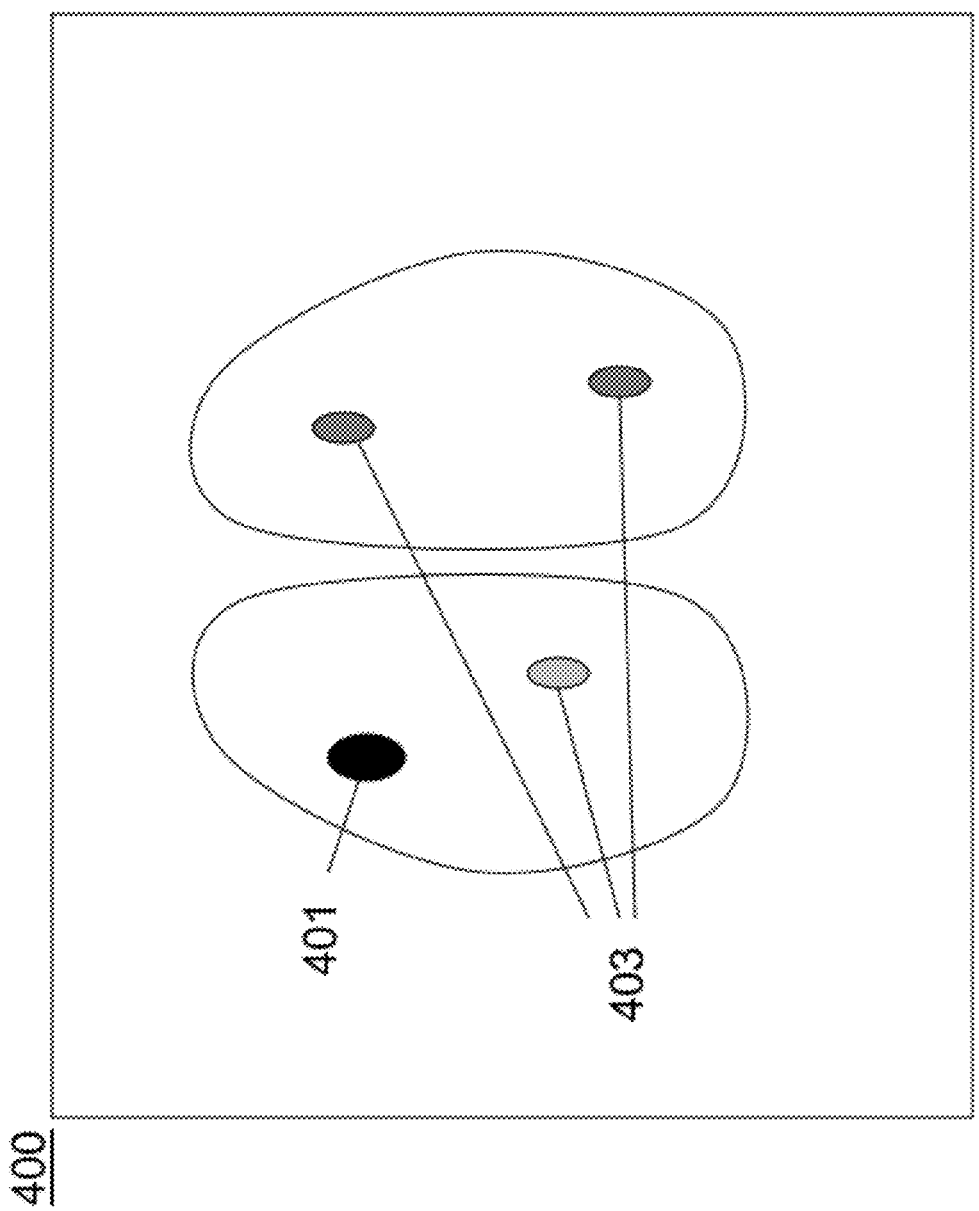

In step 307, the previous steps are repeated for additional test regions to build up the TSM. FIGS. 4A and 4B show examples of TSMs generated using the method 300. Each shows a TSM 400 of a slice of the brain. The TSM 400 includes a reference region 401. Several test regions 403 have been found to be above a threshold similarity level. The grey level of each of the test regions 403 indicates the level of similarity, with darker shading indicating a higher level of similarity.

Referring again to FIG. 3, in step 309, the generated TSM may be processed, e.g., to segment the map. In general, any image segmentation technique (manual, automatic, or hybrid) known in the art may be used (e.g., thresholding, clustering methods, histogram based methods, edge detection, neural network approaches, etc.). For example, the segmentation step may identify the edges of the test regions 403 in FIGS. 4A and 4B, or may identify a cluster of regions of interest, as shown in FIG. 4B (indicated by the dotted line).

Various embodiments may include one or more additional processing steps. For example, in some embodiments, the time resolved series of MR images may be normalized, for example, using one of the images in the series (e.g., the first image, or any other image in the series). The normalization may be carried out on a pixel by pixel basis.

In some embodiments, processing efficiency may be improved by identifying pixels having a signal to noise ration below a selected threshold, and omitting these pixels from the processing.

Referring to FIG. 5, an exemplary MRI system 500 includes an MRI imager 501 (e.g., 1.5 T Sonata MRI system, available from Siemens, Erlangen, Germany) which generates MR image data. The imager 501 is communicatively coupled to a processor 503, which receives the data from the imager 501, and process the data, using the techniques described herein (e.g., to generate a TSM). In some embodiments, imager 501 may be omitted, and processor 503 can receive data from some other source, e.g., storage memory. Processor 503 is communicatively coupled to a display 505 which displays information (e.g., a TSM) output from the processor.

In general, the techniques described herein may be used to identify tissue properties on the basis of a tissue similarity analysis. The tissue properties may include, for example, relative or absolute T2*, relative or absolute blood volume (e.g., cerebral blood volume), the presence of grey or white matter in the brain, other characteristics of tissues or blood vessels. As noted above, this information can then be used to segment the imaged area (e.g., to separate blood vessels from other tissue, to distinguish grey matter from white matter, etc.).

In various embodiments, the identified tissue properties may be used to diagnose disease or disorder, generate a treatment plan for a condition, or for any other suitable purpose. For example, as detailed in the example below, TSM techniques may be useful in the diagnosis am treatment of multiple sclerosis. As detailed below, when a known MS lesion in the brain of a subject is used as the reference region for a TSM, all other MS lesions may be readily detected in the TSM. Thus, the TSM may be used (manually or automatically) to diagnose and direct treatment to the detected MS lesions. As will be readily apparent to one skilled in the art, techniques of this type may be applied to a variety of other circumstances including, e.g., detection of tumors, detection of bleeding, detection of vascular disease, etc.

As will be understood by one skilled in the art, the techniques described herein may be extended to other contexts. For example, a similar approach may be used for estimating relative T2* and absolute T2*. For example, one may collect either spin echo or gradient echo data with more than two echo times. This gives a signal as a function of time and each pixel weighted by the spin density p and the term $\exp(-TE/T2)$ or $\exp(-TE/T2^*)$, respectively. One can process that data on a pixel-by-pixel basis to estimate either T2 or T2*. The processing can give either relative T2 or T2* or absolute T2 or T2*. An exemplary calculation is presented in the supplemental information section below. In general, this method would be applicable to any such variables where multiple time points are collected over a given parameter to evaluate relative or absolute values (just as here or with the CBV maps described herein).

Example

In this example, a processing technique of the type described above uses the original signal (rather than contrast agent concentration) from dynamic susceptibility contrast perfusion weighted imaging (PWI) to calculate a relative cerebral blood volume map and a tissue similarity map (TSM).

Ten healthy volunteers and eight multiple sclerosis (MS) patients were studied using high resolution PWI. The TSM is found by choosing a reference region in one slice and comparing its signal in a mean squared error sense to the signal from every voxel in all images throughout the brain.

As described in detail below, it was found that TSMs have high contrast and signal-to-noise ratios. The effective blood volume measured from this approach is nearly identical to that from conventional cerebral blood volume (CBV) maps. As described in detail below, advantageously, identifying one MS lesion allows for identification of nearly all lesions throughout the brain. That is, almost all MS lesions behave the same from a vascular point of view.

Dynamic susceptibility contrast (DSC) perfusion weighted imaging (PWI) is a technique that allows assessment of brain hemodynamics. It involves the utilization of signal changes that accompany the passage of a tracer through the cerebrovascular system (1-5). However, the accurate quantification of the hemodynamics of the brain is limited by the spatial resolution (6), uncertainties in arterial input function (AIF) determination (7), nonlinear ΔR2* effects and increased noise in estimating the concentration of the contrast agent (8). As described above, Tissue Similarity Map (TSM) processing approach of the type described above was applied that uses all time points (naturally accounting for multiple passes of the contrast agent) to give a new image contrast and an alternate estimate of the relative cerebral blood volume (rCBV) dependent only on the signal intensity time course s(t) and not on the concentration time curve c(t) or the need for an arterial input function. The TSM is designed to measure the likeness of the signal response from a reference region across all time points in the PWI data acquisition. Further, TSMs demonstrate the relatedness of one voxel's signal to the next, similar to the connectivity concept used in functional brain imaging (9, 10). TSM was applied to study the vascular response in lesions in multiple sclerosis (MS) subjects compared to other tissues.

Multiple sclerosis is considered a chronic inflammatory disease of the central nervous system that leads to demyelination and irreversible axonal damage (11). MS is characterized by areas of demyelinated plaques which are scattered throughout the CNS with a predilection for optic nerves, spinal cord, white matter (WM), corpus callosum, cortical and sub-cortical grey matter (GM) (12). Recently, there has been a resurgence of interest in the vascular etiology or abnormal venous vascular association with MS (14-17). There is also evidence that there is reduced perfusion as a function of the severity of the disease in MS patients, also an indicator of a vascular problem (18). In this example, TSM was used to identify those lesions linked by the same vascular response to the contrast agent in an attempt to show whether or not there is a vascular connectivity between lesions.

Ten normal volunteers aged between 23 and 56 years old were enrolled in this study. There were 6 males and 4 females; the mean age was 40.7 years. Volunteers were scanned on a 1.5 T Sonata MRI system (available from Siemens, Erlangen, Germany) with an 8-channel head coil. Parallel imaging was used with GRAPPA (generalized autocalibrating partially parallel acquisitions) and an acceleration factor of 2. The contrast agent gadolinium-DTPA (available from Magnevist, Berlex, USA) was administered with a dose of 0.1 mmol/kg of body weight and injected in a peripheral arm vein using a power injector (available from Medrad, Spectris MR Injection System, Pittsburgh, Pa., USA) at a rate of 2 ml/sec. Fifty measurements were acquired over 110 seconds. The injection of contrast agent was started at the beginning of the seventh measurement, followed immediately by a 20 ml saline flush. High resolution PWI data were obtained using a two-dimensional, single-shot, gradient echo echo-planar imaging (GE-EPI) sequence with the following imaging parameters: repetition time (TR)=2200 ms, echo time (TE)=98 ms, flip angle (FA)=60°, slice thickness (TH)=4 mm, and an inter-slice gap=4 mm. The field of view (FOV) was 256 mm×256 mm, and the acquisition matrix was 256×256 but was interpolated to 512×512 for display purposes.

The imaging protocol included T1 before contrast injection, T1 after contrast injection, T2, Magnetic Resonance Angiography (MRA) and Susceptibility Weighted Imaging (SWI) for comparison purposes. The imaging parameters for the MRA scan were: TE/TR=7/37 ms, FA=25°, slice thickness=0.8 mm, FOV=256 mm×192 mm and an acquisition matrix=512×384. The imaging parameters for the SWI scan were TE/TR=40/49 ms, FA=20°, slice thickness=2 mm, FOV=256 mm×256 mm, and an acquisition matrix=512×448. High pass filtering and phase processing were applied after image acquisition using a central matrix size of 64×64 (19). The imaging parameters for the T1 scan were TE/TR=5.26/16 ms, FA=20°, slice thickness=2 mm, Nz=104 slices, FOV=240 mm×240 mm and an acquisition matrix=512×512. The imaging parameters for the T2 scan were TE/TR=106/5230 ms, FA=160°, slice thickness=4 mm, FOV=256 mm×192 mm and an acquisition matrix=512×384.

To investigate the application of TSM in multiple sclerosis (MS), eight MS patients were recruited, six females and two males with ages from 29 to 50. The high resolution PWI data were acquired to calculate rCBV and TSM. Conventional T1, T2 and FLAIR were collected as well. The imaging parameters for the FLAIR were TE/TR=72/9970 ms, inversion time (TI)=2500 ms, FA=150°, slice thickness=4 mm with 0.4 mm gap, FOV=256 mm×192 mm, and an acquisition matrix=256×192. The parameters of PWI, T1 and T2 were as same as the normal subjects.

The paramagnetic tracer (gadolinium-DTPA) causes a change in $T_2^*$ directly in blood and indirectly in tissue when a gradient echo scan is used. The resulting signal s(t) is used as a means to measure local hemodynamic properties. Each tissue responds according to how much blood is present. In order to create the TSM, a reference region-of-interest (ROI) is selected and used as a reference input function $s_{ref}(t)$. This ROI could be a single voxel, a group of voxels or the average of all voxels. The main step is calculating a mean squared error (MSE) between $s_{ref}(t)$ and s(t) from all other voxels over n time points via:

$$MSE(\vec{r}) = \sum_{i=1}^{n} (s(\vec{r}, (t_i - \Delta ttp)) - s_{ref}(t_i))^2 \quad [1]$$

where Δttp is the difference of time-to-peak (TTP) between the voxel under investigation and the reference ROI. Tissue similarity maps can be obtained from Eq. [1] with or without the correction of time to peak. This approach will pick out all voxels with a similar temporal signal behavior. Similar tissues will theoretically have zero MSE but in the presence of noise will have a chi-squared distribution. In this work, one can attempt to null tissue representing either white matter (WM), gray matter (GM), blood vessels or lesions. If one assumes that all voxels have the same signal dependence (i.e., they are scaled only by the local blood volume), then Eq. [1] can be modified to give:

$$MSE(\vec{r}, \lambda(\vec{r})) = \sum_{i=1}^{n} (s(\vec{r}, (t_1 - \Delta ttp)) - \lambda(\vec{r}) \cdot s_{ref}(t_i))^2 \quad [2]$$

Setting the derivative of MSE(r, λ) with respect to λ(r) equal to zero gives:

$$\lambda(\vec{r}) = \frac{\sum_{i=1}^{n} (s(\vec{r}, (t_i - \Delta ttp)) \cdot s_{ref}(t_i))}{\sum_{i=1}^{n} (s_{ref}(t_i))^2} \quad [3]$$

This λ(r) map represents a ratio between a given voxel's time signal s(t) and the reference input function $s_{ref}(t)$ which gives maximum tissue similarity. In the case when all signals have the same temporal behavior; this λ(r) map can be considered a relative blood volume map called $rCBV_{TSM}$. In order to get this $rCBV_{TSM}$ map, one must do a baseline correction. The baseline value is calculated by averaging all the time points prior to injection and is referred to as $s(\vec{r}, 0)$. Then, in Eq. [3], the baseline corrected term $\Delta s(\vec{r}, t) = s(\vec{r}, 0) - s(\vec{r}, t)$ is used instead of $s(\vec{r}, t)$ to obtain the baseline corrected λ(r) map or $rCBV_{TSM}$ map.

Figure 6:
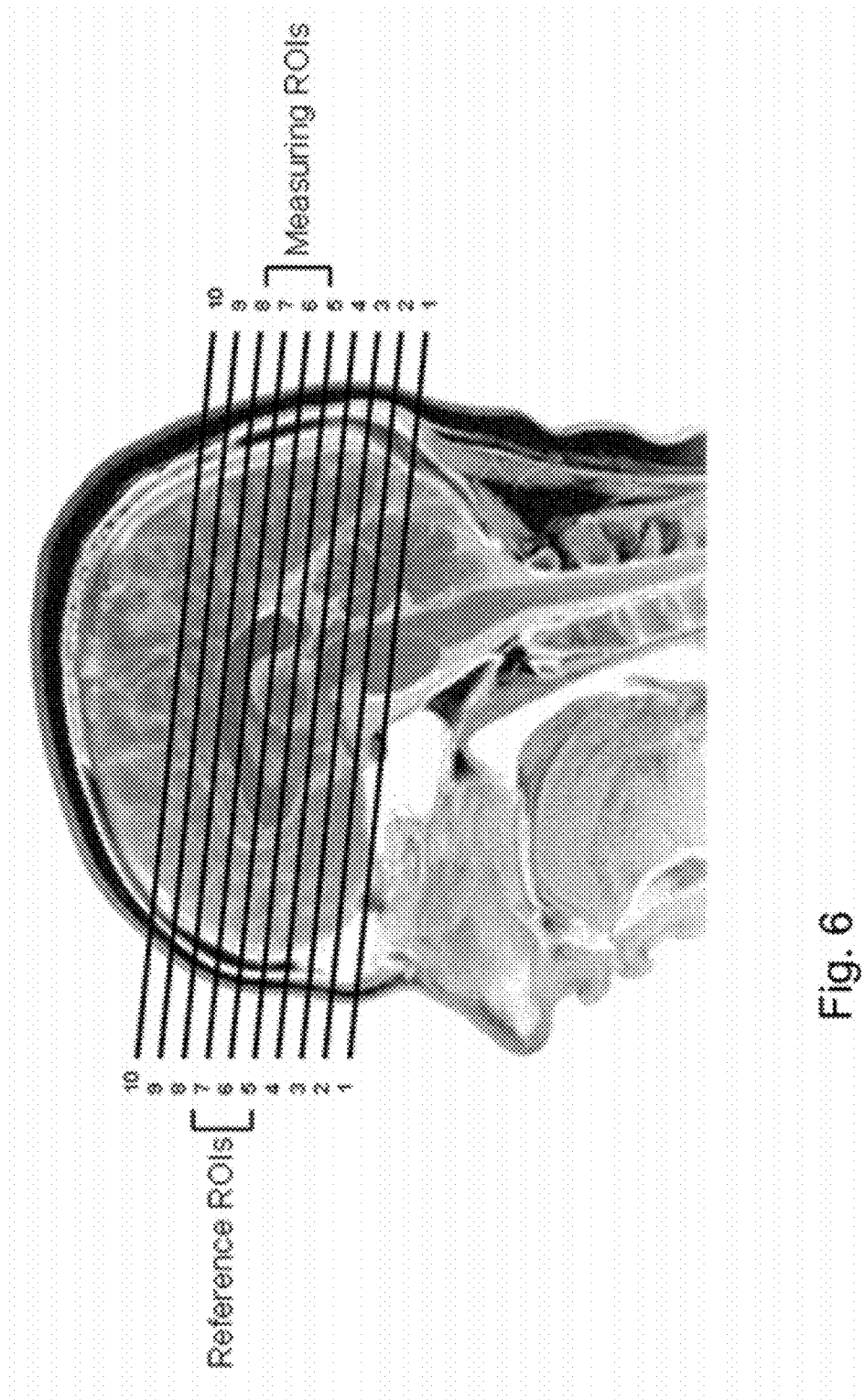
FIG. 6 illustrates PWI slice alignment and the location of the reference ROIs and measuring ROIs. The reference ROIs for a given tissue were from slices 5, 6 and 7. The measuring ROIs were from slices 5, 6, 7 and 8.
Figure 7:
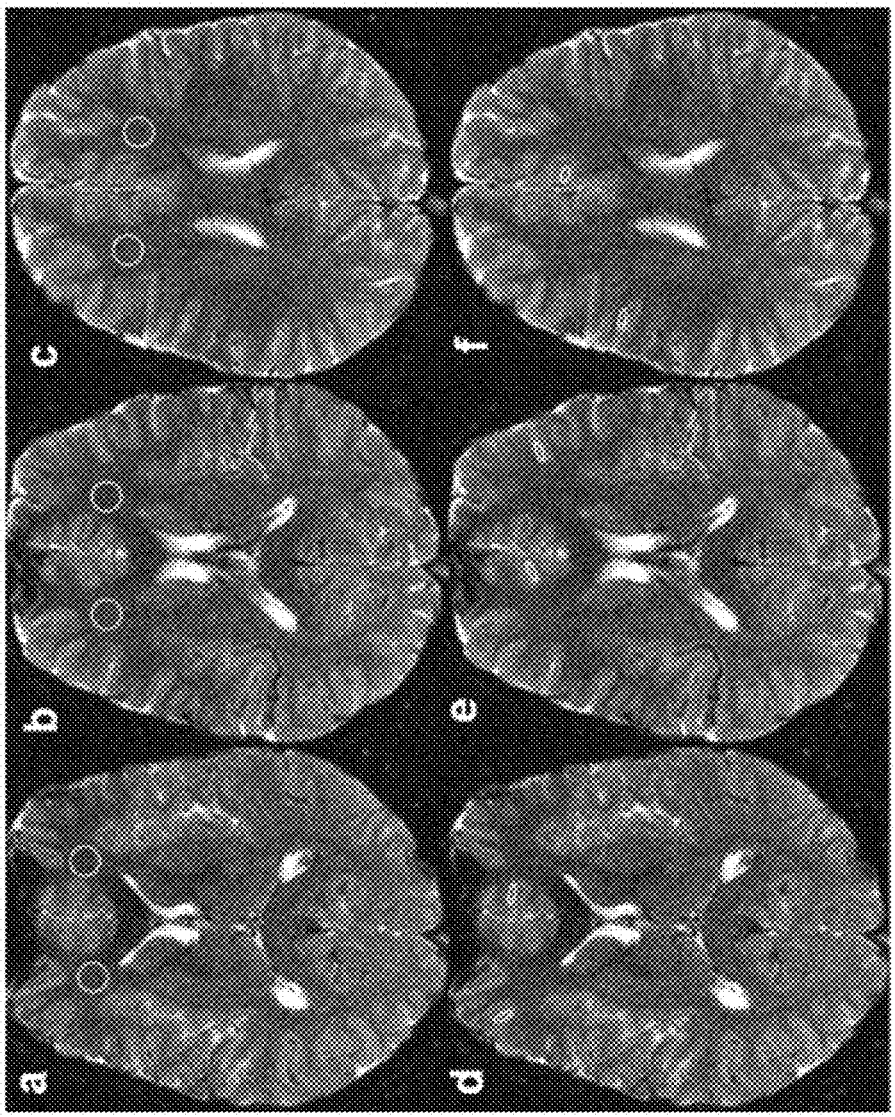
FIG. 7 illustrates reference ROIs for WM (a, b, c) and GM (d, e, f) for one subject. ROIs were from the three adjacent slices labeled 5, 6 and 7 in FIG. 6.

To evaluate the sensitivity of the method to the choice of reference region, the TSM values were measured in a given region in the brain by choosing six reference ROIs for each of WM and GM from three adjacent slices (those with the least image distortion) (see FIG. 6). In each slice, an ROI was drawn on each side of the brain for each of WM and GM. These ROIs are shown as circles in FIG. 7 but the actual ROIs were drawn inside these circles. All WM ROIs were chosen from the frontal lobe to avoid partial volume effects. This created twelve new TSMs: six nulling WM, and six nulling GM.

Figure 8:
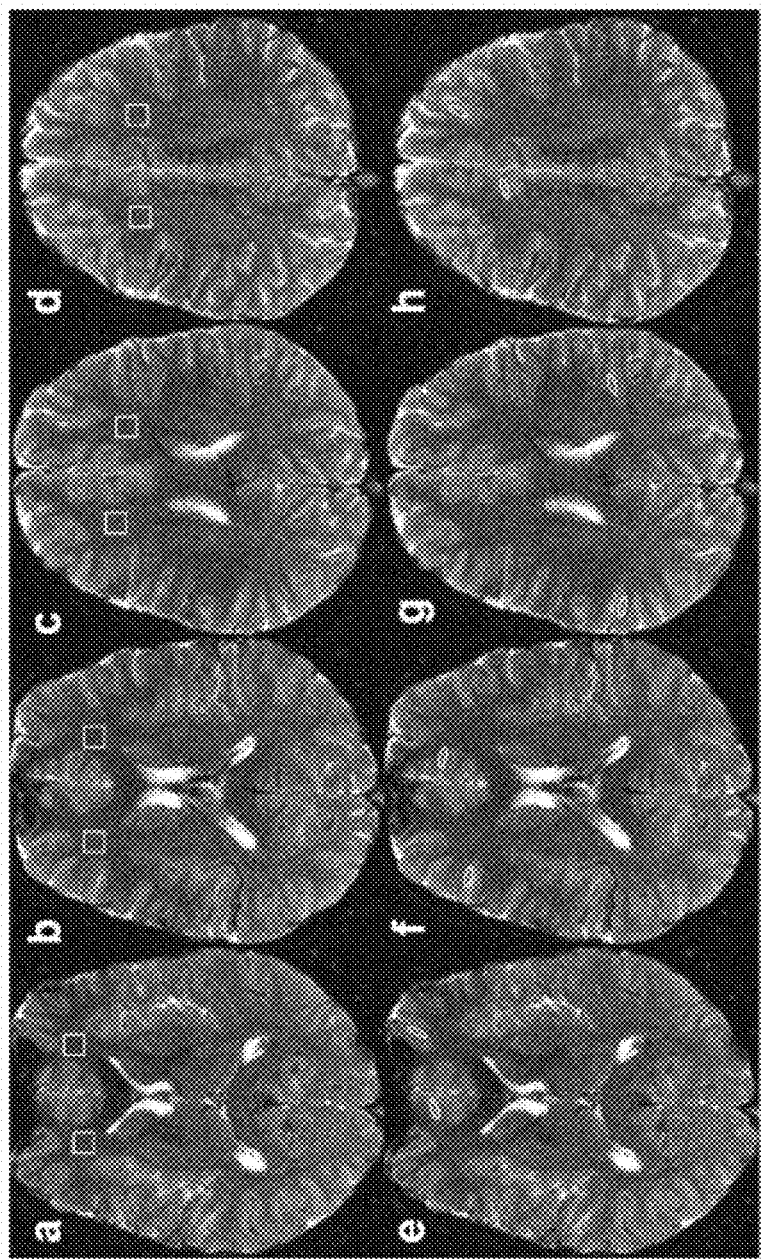
FIG. 8 illustrates measuring ROIs for WM (a, b, c, d) and GM (e, f, g, h).

Next, in order to evaluate the response of the measured TSMs to the location of the reference tissue (that is, across slices), a total of eight ROIs were chosen (referred to herein as "measuring ROIs"), two from each of four slices (the three slices mentioned above plus the next slice toward the top of the brain) for each of GM and WM. These ROIs are shown as squares in FIG. 8 but the actual ROIs were drawn inside these squares to minimize partial volume effects. These eight regions were evaluated for each of the six reference regions. Therefore, for every subject, an evaluation was performed for a total of 48 WM measurements (8×6) from TSMs nulling WM (TSM-WM) and 48 from the TSMs nulling GM (TSM-GM).

The conventional relative cerebral blood volume map (rCBVPWI) was determined by the ratio of the area under the tissue concentration-time curve and the arterial input function (AIF) (20). The AIF was automatically determined by using the maximum concentration (Cmax), time to peak (TTP) and first moment of the concentration time curve c(t) as an estimate of the mean transit time (fMTT). As the concentration time curve for an artery has short fMTT, short TTP and high Cmax, all voxels to find the best 20 voxels that meet the above criteria. Then the concentration time curves of these voxels were averaged, smoothed and truncated to avoid the second (outflow) pass of the tracer.

In the MS part of this study, the reference region was chosen to be an MS lesion, with the goal of finding out what other tissues (whether MS lesion or not) behave the same way. The number of lesions was counted in TSM-nulling lesion images (TSM-lesion) and FLAIR images for comparison studies, since FLAIR has been the routine tool in detecting lesions in MS (21-22). As the slice gap and number of slices differed between TSM-lesion and FLAIR, only matched slices (the same slice location in FLAIR and TSM-lesion images) were considered for the comparison study. Contrast-to-noise ratios (CNR) were measured in both the TSM-nulling lesion image (TSM-lesion map) and in the corresponding FLAIR image. The contrast was found from the difference between the signal of the lesion and the surrounding normal WM. The CNR from a total of 40 lesions across all the MS patients were measured.

Figure 9:
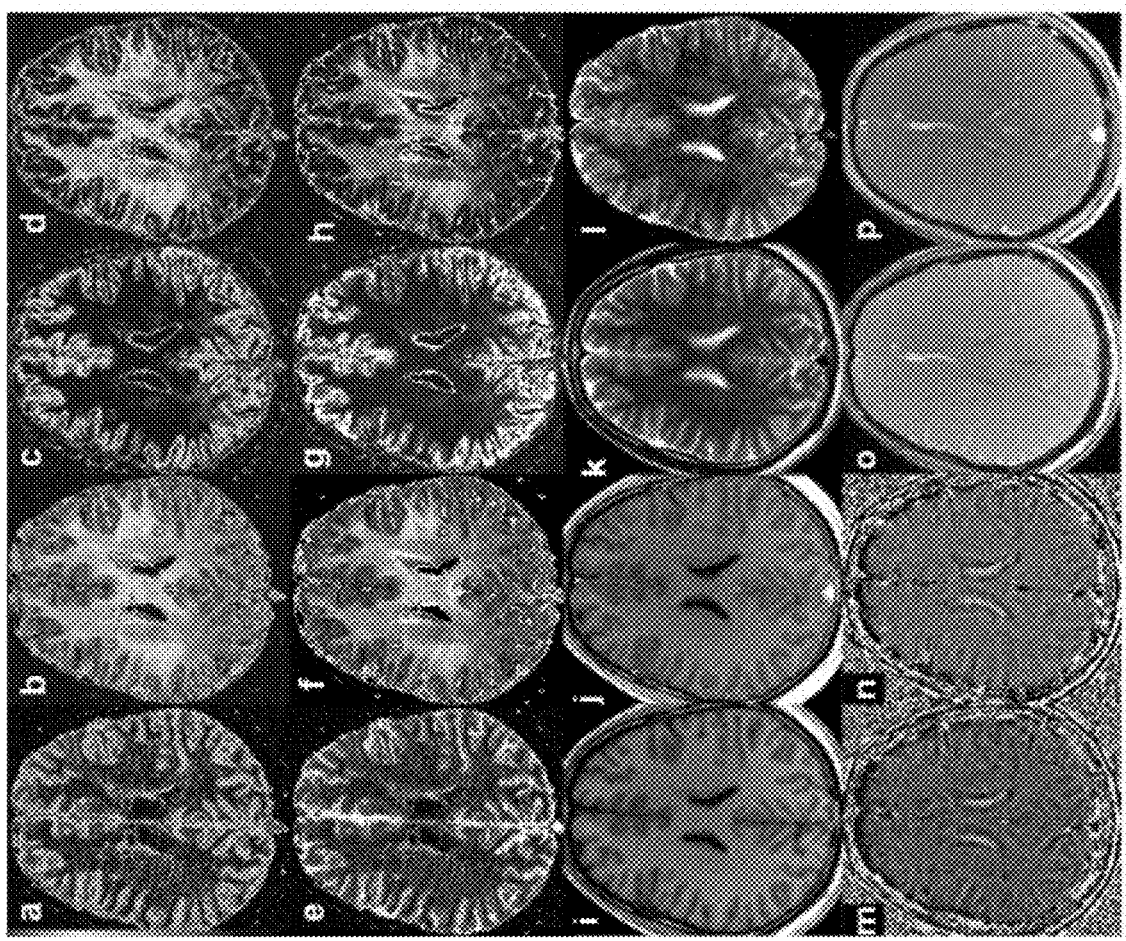
FIG. 9 shows $rCBV_{PWI}$ maps and TSM from the high resolution PWI data acquisition and processing from slice 8 of one of the volunteers. The gray scale maps are given as follows: a) and e) $rCBV_{PWI}$; b) and f) TSM-nulling blood vessel; c) and g) TSM-nulling white matter; d) and h) TSM-nulling gray matter; i) and j) are the pre and post contrast T1 images; k) is the T2 image; l) is the original PWI slice prior to contrast injection; m) and n) are the pre and post contrast SWI phase images; and o) and p) are the pre and post contrast MRA.
Figure 10:
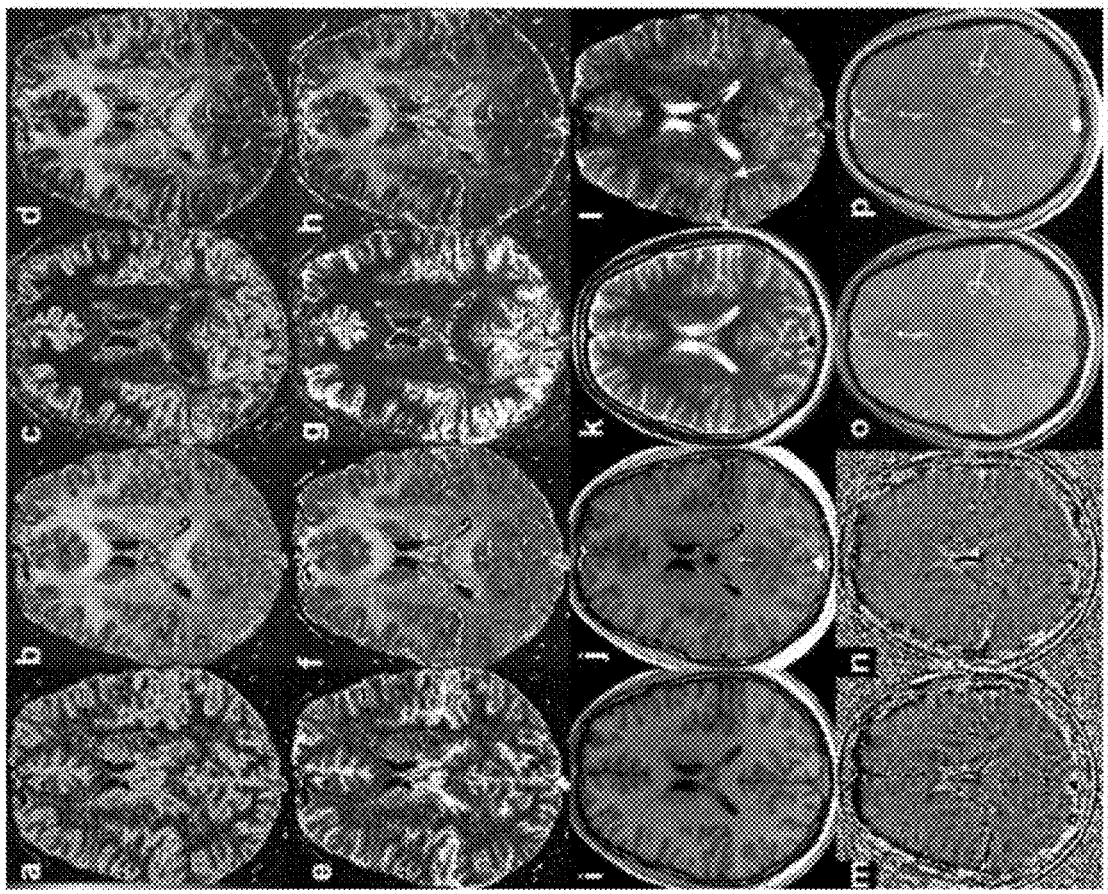
FIG. 10 shows $rCBV_{PWI}$ maps and TSM from the high resolution PWI data acquisition and processing from slice 7 of one of the volunteers. The gray scale maps are given as follows: a) and e) $rCBV_{PWI}$; b) and f) TSM-nulling blood vessel; c) and g) TSM-nulling white matter; d) and h) TSM-nulling gray matter; i) and j) are the pre and post contrast T1 images; k) is the T2 image; l) is the original PWI slice prior to contrast injection; m) and n) are the pre and post contrast SWI phase images; and o) and p) are the pre and post contrast MRA.

The high resolution PWI data were of sufficient SNR and image quality to provide excellent structural details both in the original images and in the TSMs. Using the high resolution PWI data with a TSM approach reveals for the high quality perfusion weighted images with completely new contrast mechanisms. Partial volume effects are minimized and different tissues can be easily distinguished in the TSMs. The high resolution images also made it possible to draw ROIs within a given structure easily. FIGS. 9 and 10 show a high resolution rCBVPWI map and TSMs nulling different tissues along with conventional T1, T2, SWI and MRA images from a normal healthy volunteer. The reference ROI for TSM—nulling vessel was chosen from the middle cerebral artery (MCA). In FIG. 9 (panel c), white matter was chosen as the reference ROI, so all the voxels from WM with the same signal behavior over time are suppressed. This image also demonstrates that although most WM voxels behave similarly, there are subtle differences across the slice. Unlike conventional PWI parameter maps calculated from c(t), the TSM only deals with the original s(t), so it is less noisy and can be easily used to study variations within and between tissues. Further, the summation of the signal difference over all time points endows the TSM with a higher SNR.

Figure 11:
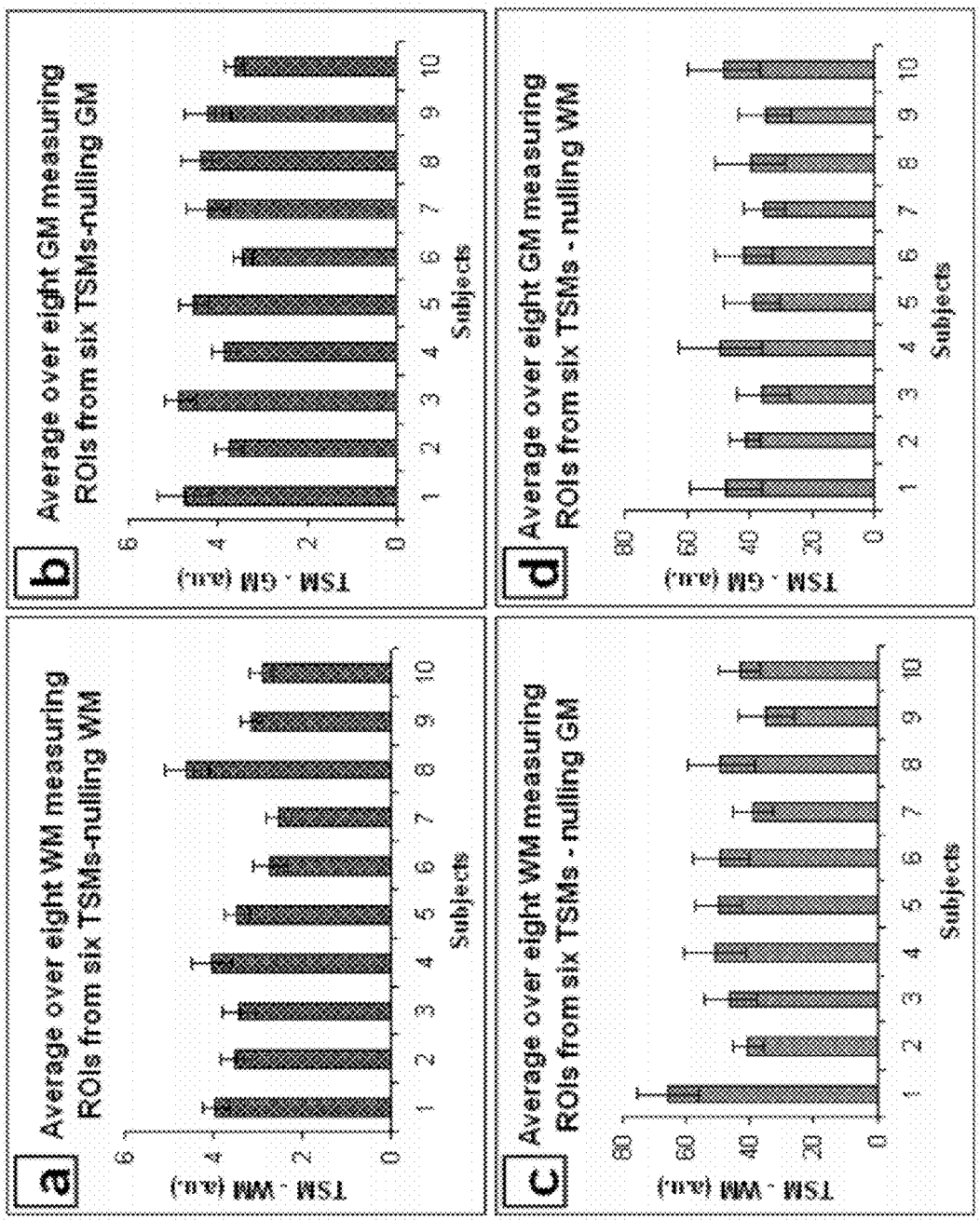
FIG. 11 shows variations of TSM in different tissues and using different reference regions for ten normal subjects: a) average over eight WM measuring ROIs from six TSMs-nulling WM; and b) average over eight GM measuring ROIs from six TSMs nulling GM. c) average over eight WM measuring ROIs from six TSMs-nulling GM; and d) average over eight GM measuring ROIs from six TSMs nulling WM. The mean and standard deviations were taken over all 48 measurements. Note the values are hovering around 4 in a and b but around 40 in c and d. Here, 4 (in arbitrary units) represents the noise level in the TSMs shown in FIGS. 9 and 10 for example.

To investigate variations of TSMs under different reference ROI selection scenarios for a given tissue type, two sets of analyses were designed. First tested was the effective nulling in the TSMs when different reference and different measuring ROIs were used. There were total 48 different measurements are made (6 different reference ROIs and 8 different measuring ROIs). In FIG. 11, most of the results yield a MSE of roughly 4 arbitrary units for WM in the TSM-WM (FIG. 11, panel a) and GM in the TSM-GM (FIG. 11, panel b). The average mean and the average standard deviations for all subjects were 3.43±0.35 and 4.16±0.38 for WM in TSMs-WM (FIG. 11, panel a) and GM in TSMs-GM (FIG. 11, panel b) respectively. Next tested was the effective stability of the signal from different GM and WM regions when WM or GM was nulled (again 6 different reference ROIs and 8 different measuring ROIs). Most of the results from subject to subject show an answer of roughly 40 arbitrary units for WM in the TSM-GM (FIG. 11, panel c) and GM in the TSM-WM (FIG. 11. panel d). The average mean and the average standard deviations for all subjects were 46.70±8.11 and 41.25±9.42 for WM in TSMs-GM (FIG. 11. panel c) and GM in TSMs-WM (FIG. 11, panel d) respectively.

Figure 12:
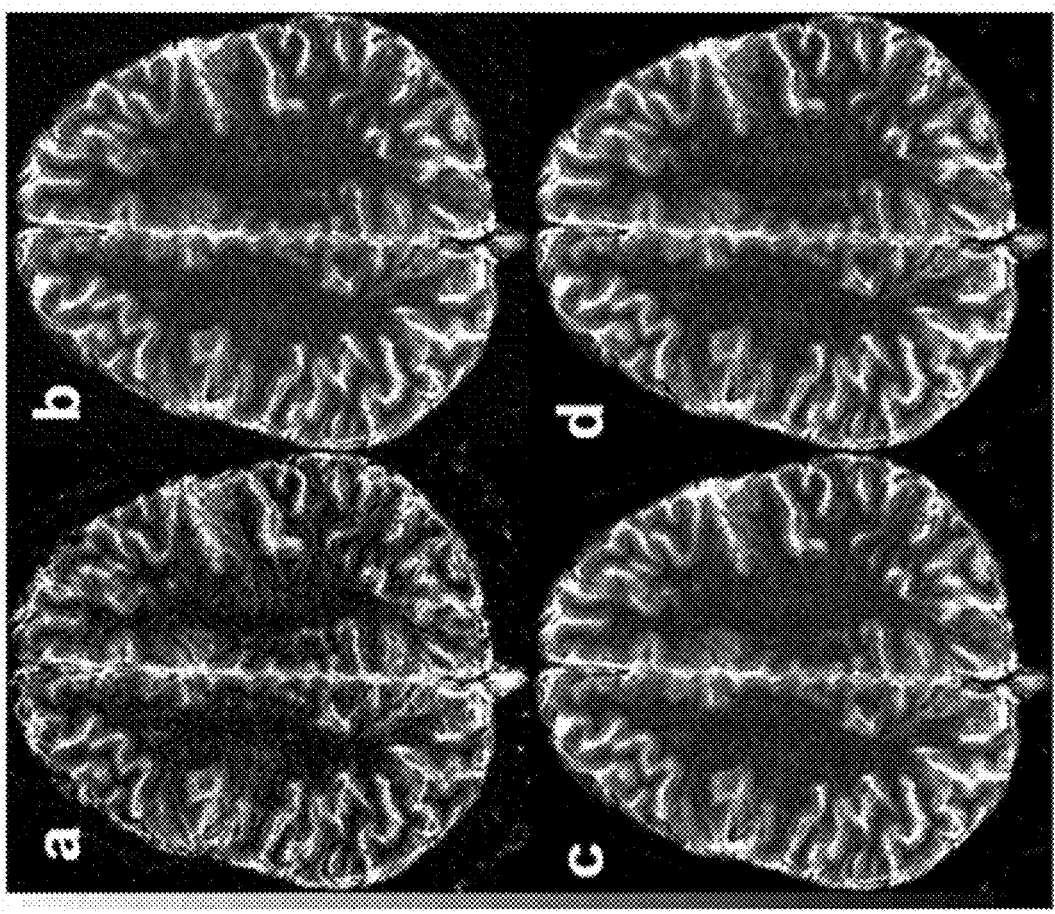
FIG. 12 shows a $CBV_{PWI}$ map from conventional method and $rCBV_{TSM}$ (or λ(r) maps) from the high resolution PWI data. a) $rCBV_{PWI}$ map; and $rCBV_{TSM}$ maps nulling: b) white matter; c) gray matter; and d) blood vessel. All $rCBV_{TSM}$ maps are independent of the reference tissues and match the $rCBV_{PWI}$ map fairly well.
Figure 13:
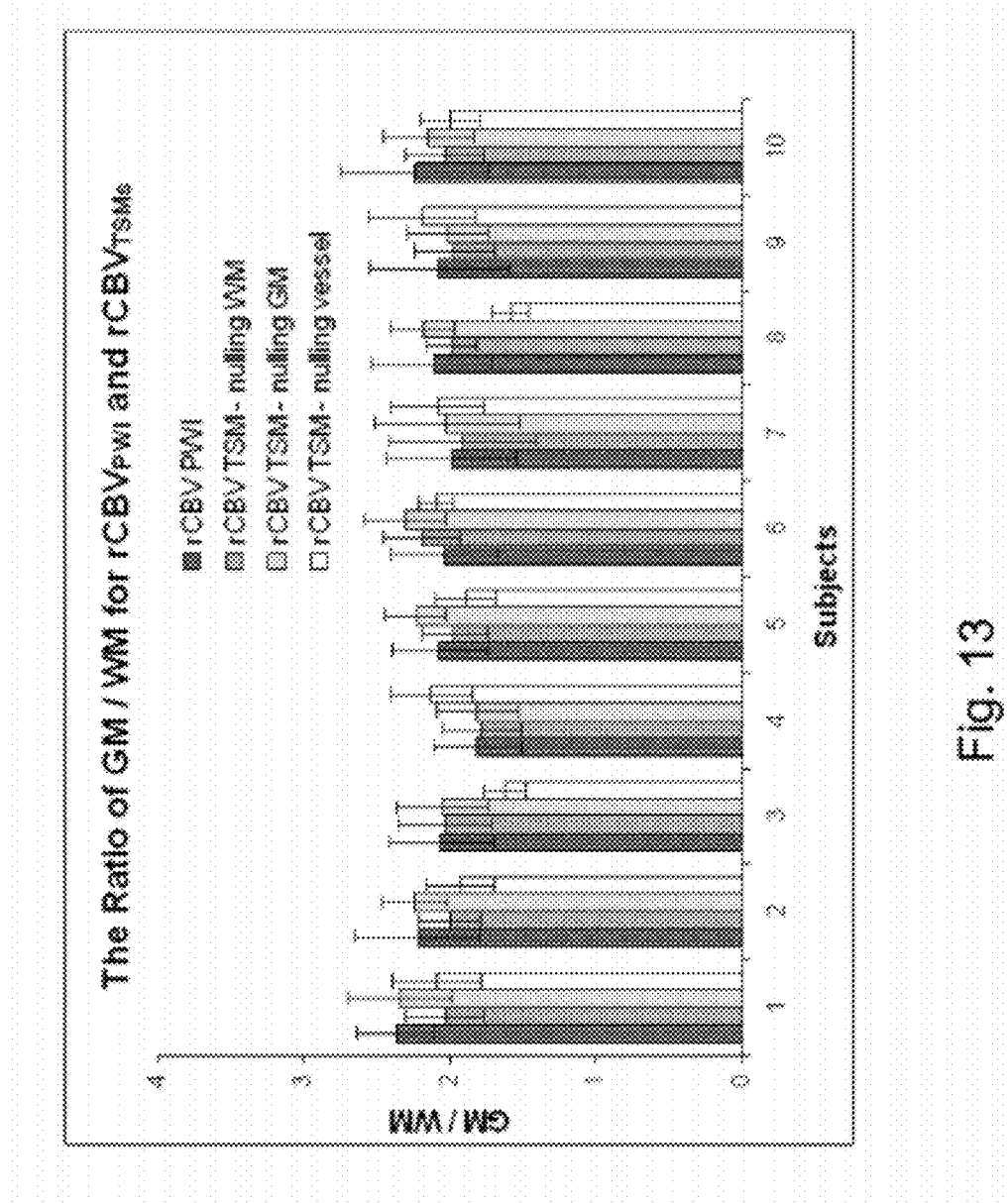
FIG. 13 shows a comparison of $rCBV_{PWI}$ from conventional method and $rCBV_{TSM}$ from TSM λ maps. Eight ROIs from GM and eight ROIs from WM were measured from $rCBV_{PWI}$, $rCBV_{TSM}$ nulling WM, nulling GM and nulling vessel. For all subjects, GM appears to have roughly twice the CBV as WM.

FIG. 12 compares the rCBVPWI map from conventional methods with the rCBVTSM from λ(r) maps for the different TSM nulling approaches. The rCBVTSM maps from WM (panel b), GM (panel c), or blood vessels (panel d) as the reference region were identical apart from a scale factor, as expected. The SNR of the rCBVTSM map is better than the paired rCBVPWI map (FIG. 13, panel a) from the usual PWI analysis. To validate whether the rCBVTSM map is a viable alternate method to quantify relative cerebral blood volume, average value was measured for eight GM ROIs and eight WM ROIs for rCBVPWI and for rCBVTSM from nulling WM, GM and blood vessels. FIG. 13 illustrates the GM values over the WM values from these four maps for each subject. The means and standard deviations of the ratios of GM over WM over the ten subjects were 2.10±0.38 for the conventional rCBVPWI map and 1.99±0.27, 2.13±0.29 and 1.96±0.23 for the rCBVTSM maps from nulling WM, GM and blood vessel respectively.

Signal-to-noise ratios (SNR) for the rCBVPWI map, rCBVTSM maps from nulling WM, GM and blood vessel were measured from eight ROIs of WM and eight ROIs of GM. In order to get large and homogeneous GM ROIs, ROIs were chosen from the caudate, putamen, globus palidus and thalamus. The average SNRs over 10 subjects for all regions were: 2.7, 5.0, 4.9 and 4.9 for rCBVPWI map, rCBVTSM maps from nulling WM, GM and blood vessel, respectively. On average, the rCBVTSM maps show an increased in SNR of 82% over the conventional rCBVPWI.

Figure 14:
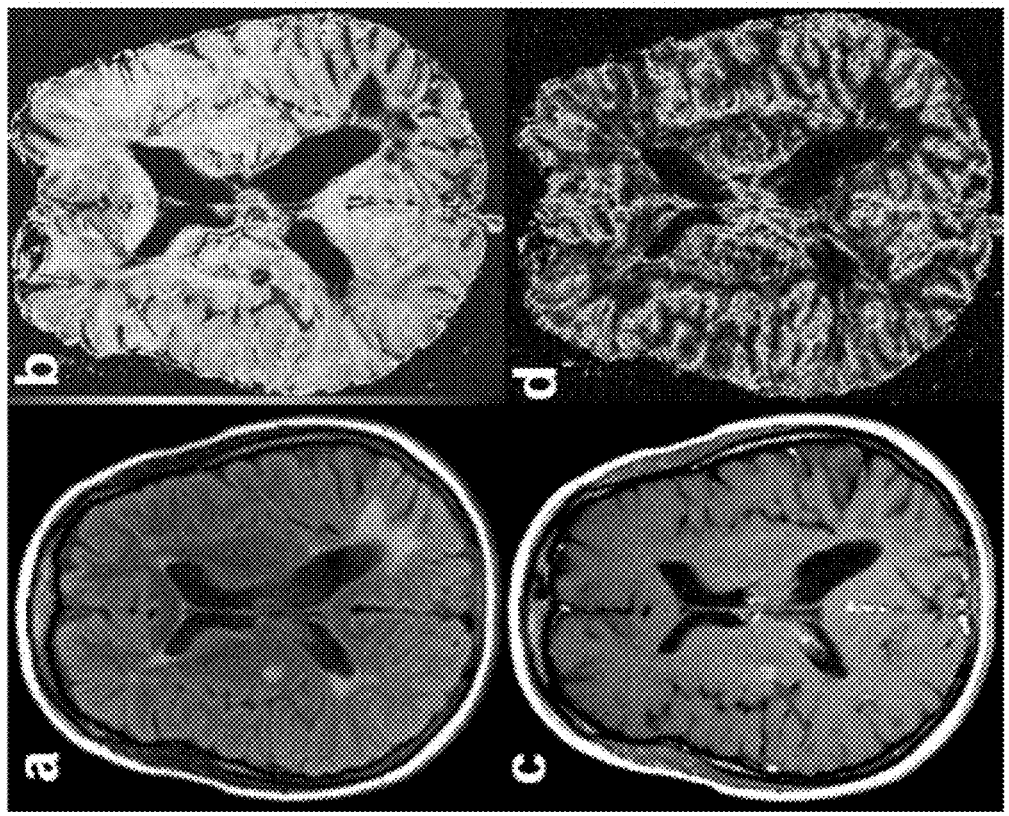
FIG. 14 shows MS lesions for one patient. a) FLAIR; b) TSM-nulling lesion; c) post-contrast T1 weighted imaging; d) rCBV from conventional method. The thin arrows point the chronic lesions in FLAIR (a) and TSM (b). The lesion pointed by bold arrow is acute as seen enhanced in post-contrast T1 (c).
Figure 15:
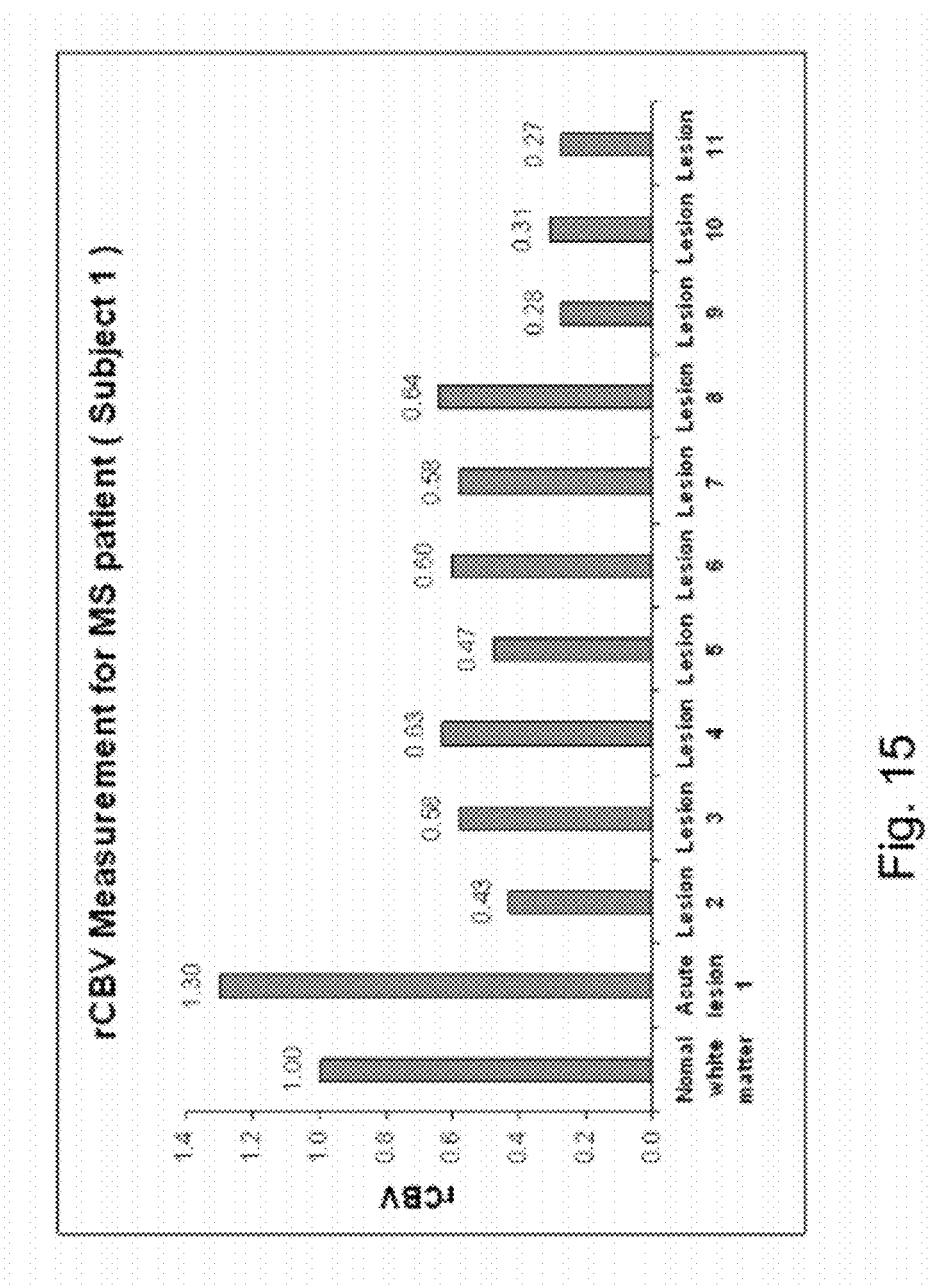
FIG. 15 shows an rCBV comparison between normal WM and MS lesions of subject 1. The data were normalized so that normal appearing white matter was given the value of exactly unity. All MS lesions were found to have a smaller than normal CBV relative to WM except for the one acute lesion.

The TSM approach resulted in enhancing MS lesions for all eight patients with high signal-to-noise ratio, no matter which lesion is chosen as the reference ROI. The TSM-lesion map picked up both chronic and acute lesions throughout the brain (FIG. 14). In the TSM-lesion and FLAIR comparison, the TSM-lesion image picked up 95% of lesions with respect to FLAIR. The 5% difference might have been due to slice gap variation between FLAIR and TSM-lesion images. The lesions observed in the TSM-lesion images (FIG. 14, panel a) were of similar size and shape as those in FLAIR (FIG. 14, panel b). Among all these lesions, only one gadolinium-enhanced lesion was visible (indicated by a bold arrow FIG. 14, panel c) in the T1 post-contrast image. As the lesions are not clearly visible in the rCBV maps (FIG. 14, panel d), the TSM-lesion image made it possible to draw the boundary of the lesion and to copy the boundary to rCBV maps for quantification. For the same subject as shown in FIG. 14, ten of the lesions were chronic and showed less rCBV than white matter (FIG. 15). The average rCBV for these ten lesions relative to normal appearing white matter was 0.48 (i.e., the lesions had a lower relative CBV than WMI). The acute lesion (bold arrow indicated in FIG. 14, panel c) had 30% higher rCBV than the normal white matter. The CNRs between lesions and WM in FLAIR and those seen in the TSMs—nulling lesion were measured in 40 lesions over all subjects. The average CNRs were 15.87×22/15 for TSM and 7.38× roughly 4 for FLAIR, respectively.

The variations of the TSMs from different reference ROIs and from different measuring ROIs across slices were evaluated in our study. Theoretically, the WM tissue in TSM-WM should be zero. However in the presence of noise in the image, the mean square error measure will generate an average response of $n\sigma^2$ where $\sigma$ is the standard deviation of the noise in the original image. With a standard deviation of roughly 28 for the noise, $n\sigma^2$ is roughly 39200. After normalization by 10000, the MSE is roughly 4 as was seen in FIG. 11 (panel a) and FIG. 11 (panel b). It is also of interest to evaluate the TSM response for one tissue when another tissue is nulled. Excellent CNR was observed between GM and WM when the GM is nulled as shown in FIG. 9 (panel h) and FIG. 10 (panel 5*h*). The average CNR between WM and GM was found to be roughly 10:1. Therefore, it may be possible to consider segmenting these images themselves rather than using conventional T1 or T2 images.

Veins have shorter T2* than arteries; they tend to lose the signal in the long echo time scans (especially for large veins). Our high resolution PWI data were collected with an echo time of 98 ms. In FIG. 5*l* (the PWI image), it was observed that the vein indicated by the arrow had low signal even before the bolus arrival. Therefore, this vein appears bright in FIG. 5*f*.

The $rCBV_{TSM}$ maps from the TSM approach were shown to match those obtained from the usual DSC PWI rCBV calculations. The images show an overall similarity between the two methods. The SNR measured in WM for the $rCBV_{TSM}$ maps (nulling WM, GM and blood vessel) was 5.3, while that from the $rCBV_{PWI}$ map was 2.7. Similar measures in the caudate, putamen, globus palidus and thalamus for GM were 4.6 from the $rCBV_{TSM}$ maps and 2.5 from the $rCBV_{PWI}$ map.

Subtle variations were observed in WM tissue response across the brain when GM is nulled. For example, in FIG. 9 (panels d, h) and FIG. 10 (panels d, h) there is a darker response for WM in the corona radiata region, and also WM appears to decay to smaller values from anterior to posterior especially in younger individuals. In the older individuals, this variation was not clear.

In this example, obtaining accurate blood volumes for WM is very difficult, if not impossible, on a voxel-by-voxel basis because the data are so noisy. The use of a tissue similarity map offers an approach that uses all time points in a way that enhances the SNR in the output images. This may offer an avenue to differentiate more subtle effects related to flow variations within a tissue than can be seen otherwise with conventional CBF or CBV maps. This increase in sensitivity may help in better diagnosing the affected tissue in diseases.

The noise was difficult to measure for FLAIR. The lowest variation in the standard deviation was found to be dependent on the signal amplitude so as the amplitude increased so did the variation. These values ranged from 5 to 12 in the tissue and 22 outside the brain. To be conservative, 5 was used in estimates for the CNR for FLAIR but practically the CNR may well be less than this by as much as a factor of 2 to 4. The larger noise outside may be from motion artifacts or parallel imaging effects. The TSM maps obeyed the Rayleigh distribution fairly well in the lesion which was chosen as the reference region. The conclusion regarding contrast is that they are in fact quite similar between the two methods with TSM perhaps carrying an advantage in some cases.

In summary, it was found that almost all MS lesions appear to have the same vascular response. This adds further evidence to the camp suggesting a vascular etiology or at least a vascular mechanism to multiple sclerosis. In general, it appears that TSMs are a very useful tool to reveal information about tissues otherwise difficult to see with conventional PWI processing. This tool may be used in validation and diagnosis of the vascular similarities in diseases, such as multiple sclerosis, stroke or tumor.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Supplemental Information

The following illustrates an exemplary calculation of the type described in paragraph 0080 of the specification.

Signal from Referenced ROI:

$$S_{ref}(t) = \rho_{ref} e^{-R2^*_{ref}t} \quad S_{ref}(0) = \rho_{ref}$$

Signal from each voxel:

$$S_t(t) = \rho_t e^{-R2^*_t t} \quad S_t(0) = \rho_t$$

Calculation of MSE $$MSE \propto \sum_{TE_1}^{TE_n} (\rho_t e^{-R^*_{2t}TE_1} - \lambda_{mixed} \rho_{ref} e^{-R^*_{2ref}TE_1})^2$$

Calculation of MSE' to get mixed_spin density_T2* effect map $$MSE' \propto \left[\sum_{TE_1}^{TE_n} (\rho_t e^{-R^*_{2t}TE_1} - \lambda_{mixed} \rho_{ref} e^{-R^*_{2ref}TE_1})^2\right]' = 0$$

Here $\Delta t = TE_{1+1} - TE_1$;
n is echo number $$\lambda_{mixed} = \frac{\rho_t}{\rho_{ref}} e^{(R^*_{2ref} - R^*_{2t})TE_1} \frac{(1-e^{-2R^*_{2ref}\Delta t})(1-e^{-(R^*_{2ref}+R^*_{2t})\Delta t \cdot n})}{(1-e^{-(R^*_{2ref}+R^*_{2t})\Delta t})(1-e^{-2R^*_{2ref}\Delta t \cdot n})}$$

$$= \frac{S_t(TE_1)}{S_{ref}(TE_1)} \cdot \frac{(1-e^{-2R^*_{2ref}\Delta t})(1-e^{-(R^*_{2ref}+R^*_{2t})\Delta t \cdot n})}{(1-e^{-(R^*_{2ref}+R^*_{2t})\Delta t})(1-e^{-2R^*_{2ref}\Delta t \cdot n})}$$

This is the theoretical solution to $\lambda_{mixed}$ which is also calculated from the original data itself and set equal to this expression.

Normalization to remove the spin density effects $$MSE' \propto \left[\sum_{TE_1}^{TE_n} \left(\frac{\rho_t e^{-R^*_{2t}TE_1}}{\rho_t e^{-R^*_{2t}TE_1}} - \lambda_{nor-relR^*_2} \frac{\rho_{ref} e^{-R^*_{2ref}TE_1}}{\rho_{ref} e^{-R^*_{2ref}TE_1}}\right)^2\right]' = 0$$

$$\lambda_{nor-relR^*_2} = \frac{(1-e^{-2R^*_{2ref}\Delta t})(1-e^{-(R^*_{2ref}+R^*_{2t})\Delta t \cdot n})}{(1-e^{-2R^*_{2ref}\Delta t \cdot n})(1-e^{-(R^*_{2ref}+R^*_{2t})\Delta t})} = \lambda_{mixed} \frac{S_{ref}(TE_1)}{S_t(TE_1)}$$

Here the known variables are: $R_{2^*ref}$, $\Delta t$, n, $\lambda_{nor-relR2}*$
Unknown variable is $R_{2^*t}$
for each guessed $R_{2^*t}$, one obtains $\lambda'_{nor-relR2*}$
If $|\lambda nor-relR2^* - \lambda nor-relR2^*|$ reaches the minimum, one obtains R2*t or T2*t

REFERENCES

It is to be understood that the list of references below does not constitute an admission that any of the references are prior art.

1. Wittsack H J, Ritzl A, Fink G R, et al. MR Imaging in Acute Stroke: Diffusion-weighted and Perfusion Imaging Parameters for Predicting Infarct Size. Radiology 2002; 222:397-403.
2. Boxerman J L, Schmainda K M, Weisskoff R M. Relative cerebral blood volume maps corrected for contrast agent extravasation significantly correlate with glioma tumor grade, whereas uncorrected maps do not. AJNR Am J Neuroradiol 2006; 27:859-867.
3. Ge Y, Law M, Johnson G, et al. Dynamic Susceptibility Contrast Perfusion MR Imaging of Multiple Sclerosis Lesions: Characterizing Hemodynamic Impairment and Inflammatory Activity. AJNR Am J Neuroradiol 2005; 26:1539-1547.
4. Kinuya K, Kakuda K, Nobata K, et al. Role of brain perfusion single-photon emission tomography in traumatic head injury. Nucl Med Commun 2004; 25:333-337.
5. Harris G J, Lewis R F, Satlin A, et al. Dynamic susceptibility contrast MR imaging of regional cerebral blood volume in Alzheimer disease: a promising alternative to nuclear medicine. AJNR Am J Neuroradiol 1998; 19:1727-1732.
6. Chen J J, Smith M R, Frayne R. The Impact of Partial-Volume Effects in Dynamic Susceptibility Contrast Magnetic Resonance Perfusion Imaging. J Magn Reson Imaging. 2005; 22:390-399.
7. Lorenz C, Benner T, Lopez C J, et al. Effect of Using Local Arterial Input Functions on Cerebral Blood Flow Estimation. J Magn Reson Imaging. 2006; 24:57-65.
8. Calamante F, Connelly A, van Osch M J P. Nonlinear ΔR2* Effects in Perfusion Quantification Using Bolus-Tracking MRI. MRM 2009; 61:486-492.
9. Biswal B, Yetkin F Z, Haughton V M, Hyde J S. Functional connectivity in the motor cortex of resting human brain using echo-planar. MRI. Magn. Reson. Med. 1995; 34:537-541.
10. Barry Horwitz. The elusive concept of brain connectivity. NeuroImage 2003; 19:466-470.
11. Lucchinetti C F, Bruck W, Rodriguez M, et al. Distinct patterns of multiple sclerosis pathology indicates heterogeneity in pathogenesis. Brain Pathol 1996; 6:259-274.

12. Lassmann H. Pathology of Multiple Sclerosis. In McAlpine's Multiple Sclerosis, Compston A, Ebers G, Lassmann H, McDonald W I, Matthews B, Wekerle H (eds). Churchill Livingstone: London, 1998.
13. Putnam T J. Studies in multiple sclerosis: encephalitis and sclerotic plaques produced by venular obstruction. Arch of neuronal and Psych 1935; 33:929-940.
14. Rashid W, Parkes L M, Ingle G T, et al. Abnormalities of cerebral perfusion in multiple sclerosis. J Neurol Neurosurg Psychiatry 2004; 75(9):1288-1293.
15. Wuerfel J, Bellmann-Strobl J, Brunecker P, et al. Changes in cerebral perfusion precede plaque formation in multiple sclerosis: a longitudinal perfusion MRI study. Brain 2004; 127(1):111-119.
16. Adhya S, Johnson G, Herbert J, et al. Pattern of hemodynamic impairment in multiple sclerosis: dynamic susceptibility contrast perfusion MR imaging at 3.0 T. Neuroimage 2006; 33(4):1029-1035.
17. Inglese M, Park S J, Johnson G, et al. Deep gray matter perfusion in multiple sclerosis: dynamic susceptibility contrast perfusion magnetic resonance imaging at 3 T. Arch Neurol 2007; 64(2):196-202.
18. Law M, Saindane A M, Ge Y, et al. Microvascular Abnormality in Relapsing-Remitting Multiple Sclerosis: Perfusion MR Imaging Findings in Normal-appearing White Matter. Radiology 2004:645-652.
19. Haacke E M, Xu Y B, Cheng Y C, Reichenbach J R. Susceptibility Weighted Imaging (SWI). Magn Reson Med 2004; 52:612-618.
20. Ostergaard L. Principles of cerebral perfusion imaging by bolus tracking. J Magn Reson Imaging, 2005; 22:710-717.
21. Neema M, Stankiewicz J, Arora A, et al. MRI in multiple sclerosis: what's inside the toolbox? *Neurotherapeutics* 2007; 4:602-17.
22. Bakshi R, Thompson A J, Rocca M A, et al. MRI in multiple sclerosis: current status and future prospects. *Lancet Neurol* 2008; 7:615-25.
23. Wiart M. et al. Perfusion-Based Segmentation of the Human Brain Using Similarity *Mapping. Magnetic Resonance in Medicine* 45:261-268 (2001)
24. Rogowska, J. Applications of Similarity Mapping in Dynamic MRI. *IEE TRANSACTIONS ON MEDICAL IMAGING*, VOL. 14, NO. 3, SEPTEMBER 1995

What is claimed is:

1. A method comprising:
   receiving a time resolved series of magnetic resonance (MR) images of an imaged region of a subject;
   identifying a spatial region within at least one of the MR images as a reference region, the reference region corresponding to a first tissue type;
   computing a signal difference metric based on differences, over at least a subset of the time resolved MR images, between a signal associated with the reference region and another signal associated with at least one other region of the MR images;
   determining a relative tissue property parameter that minimizes the signal difference metric; and
   generating a tissue property similarity map based on the relative tissue property parameter, the tissue property similarity map indicative of similarity in tissue property between the reference region and the at least one other region.

2. The method of claim 1, wherein the time resolved series of MR images comprises a time resolved series of MR images collected at respective times.

3. The method of claim 1, further comprising:
   generating the time resolved series MR images by:
   receiving MR magnitude, phase, or magnitude and phase data related to the imaged region of the subject at a series of times; and
   for each time of the series of times, Fourier transforming the corresponding data to generate an image in the series of MR images.

4. The method of claim 1 wherein each of the MR images are generated using a gradient echo based imaging sequence, and the time resolved series of MR images are acquired at intervals corresponding to the echo time of the imaging sequence.

5. The method of claim 4, wherein the gradient echo based imaging sequence comprises a sequence obtained from at least one of: an echo planar scan and a gradient echo scan.

6. The method of claim 1, wherein computing the signal difference metric comprises:
   selecting one or more image pixels in the reference region;
   storing temporally resolved reference pixel data for the selected one or more image pixels; and
   computing differences between temporally resolved pixel data of one or more other pixels and the stored temporally resolved reference pixel data.

7. The method of claim 1, wherein the tissue property similarity map is generated using a limited temporal window.

8. The method claim 1, wherein the time resolved series of MR images corresponds to a series generated from a gradient echo scan.

9. The method of claim 1, wherein the MR images comprise information related to local blood vessel volume in the imaged region.

10. The method of claim 1, further comprising generating information indicative of at least one of: relative local blood volume, absolute $T2^*$, and relative $T2^*$ based on the generated similarity map.

11. The method of claim 1, further comprising:
    receiving reference $T2^*$ information indicative of $T2^*$ for at least one pixel in the time resolved series of MR images; and
    generating information indicative of relative $T2^*$ based on the tissue property similarity map and the reference $T2^*$ information.

12. The method of claim 1, wherein generating the tissue property similarity map comprises:
    selecting at least one reference pixel from the reference region;
    computing the relative tissue property parameter for each of substantially all of the remaining pixels in the series of MR images; and
    generating similarity information for each of substantially all of the remaining pixels in the series of MR images based on the relative tissue property parameter.

13. The method of claim 1 wherein computing the relative tissue property parameter comprises:
    determining at least one low signal pixel in the series of MR images having a signal to noise ratio below a threshold level; and
    omitting the at least one low signal pixel from the computation of the relative tissue property parameter.

14. The method of claim 1 further comprising: comparing one or more values associated with the tissue property similarity map to a threshold.

15. The method of claim 1, wherein the reference region corresponds to an abnormal region of the imaged region.

16. The method of claim 1, further comprising:
    based on the tissue property similarity map, generating tissue property information indicative of a property of tissue in the imaged region of the subject.

17. The method of claim 16, wherein the tissue property comprises at least one of: T2*, relative blood volume, relative cerebral blood volume, the presence of a blood vessel, and the presence of a selected tissue type.

18. The method of claim 1, further comprising:
normalizing each image in the time resolved series of MR images based on at least one reference image in the series.

19. The method of claim 18, wherein the normalization is carried out on a pixel by pixel basis.

20. The method of claim 19, wherein the reference image is the temporally first image in the series.

21. A system comprising:
a processor configured to receive magnetic resonance (MR) image data and process the MR image data using a method comprising;
receiving a time resolved series of MR images of an imaged region of a subject;
identifying a spatial region within at least one of the MR images as a reference region, the reference region corresponding to a first tissue type;
computing a signal difference metric based on differences, over at least a subset of the time resolved MR images, between a signal associated with the reference region and another signal associated with at least one other region of the MR images;
determining a relative tissue property parameter minimizing the signal difference metric; and
generating a tissue property similarity map based on the relative tissue property parameter, the tissue property similarity map indicative of similarity in tissue property between the reference region and the at least one other region.

22. A computer program product, comprising a non-transitory computer usable medium having a computer readable program code embodied therein, said computer readable program code adapted to be executed to implement a method comprising:
receiving a time resolved series of magnetic resonance (MR) images of an imaged region of a subject;
identifying a spatial region within at least one of the MR images as a reference region, the reference region corresponding to a first tissue type;
computing a signal difference metric based on differences, over at least a subset of the time resolved MR images, between a signal associated with the reference region and another signal associated with at least one other region of the MR images;
determining a relative tissue property parameter that minimizes the signal difference metric; and
generating a tissue property similarity map based on the relative tissue property parameter, the tissue property similarity map indicative of similarity in tissue property between the reference region and the at least one other region.

* * * * *